United States Patent
Sipione et al.

(10) Patent No.: US 9,023,812 B2
(45) Date of Patent: May 5, 2015

(54) NEUROPROTECTIVE GANGLIOSIDE COMPOSITIONS FOR USE IN TREATING HUNTINGTON'S DISEASE

(75) Inventors: Simonetta Sipione, Edmonton (CA); Vittorio Maglione, Edmonton (CA)

(73) Assignee: The Governors of the University of Alberta, Edmonton (CA)

( * ) Notice: Subject to any disclaimer, the term of this patent is extended or adjusted under 35 U.S.C. 154(b) by 127 days.

(21) Appl. No.: 13/394,106

(22) PCT Filed: Aug. 20, 2010

(86) PCT No.: PCT/CA2010/001282
§ 371 (c)(1), (2), (4) Date: May 29, 2012

(87) PCT Pub. No.: WO2011/026216
PCT Pub. Date: Mar. 10, 2011

(65) Prior Publication Data
US 2012/0283199 A1    Nov. 8, 2012

Related U.S. Application Data

(60) Provisional application No. 61/239,953, filed on Sep. 4, 2009.

(51) Int. Cl.
A61K 31/7032    (2006.01)
G01N 33/68    (2006.01)
A61K 9/00    (2006.01)

(52) U.S. Cl.
CPC ........ *A61K 31/7032* (2013.01); *G01N 33/6896* (2013.01); *A61K 9/0085* (2013.01); *G01N 2800/2835* (2013.01)

(58) Field of Classification Search
None
See application file for complete search history.

(56) References Cited

FOREIGN PATENT DOCUMENTS

| EP | 0373039 A2 | 6/1990 |
| WO | 03017949 A2 | 3/2003 |
| WO | 2004080960 A3 | 9/2004 |

OTHER PUBLICATIONS

Desplats et al., Neurobiol. Dis., 2007, 27, p. 265-277, published form.*
Svennerholm et al., Dementia Geriatr. Cognit. Disord., 2002, 14(3), p. 128-136.*
Giralt et al., Journal of Huntington's Disease, 2012, 1, p. 155-173.*
Copy of International Preliminary Report on Patentability dated Mar. 6, 2012 issued in PCT/CA2010/001282.
Copy of International Search Report and Written Opinion dated Nov. 24, 2010 issued in PCT/CA2010/001282.
Desplats et al., Glycolipid and ganglioside metabolism imbalances in Huntington's disease. Neurobiol Dis. Sep. 2007;27(3):265-277.
Dunbar et al., Neurotrophic Enhancers as Therapy for Behavioral Deficits in Rodent Models of Huntington's Disease: Use of Gangliosides, Substituted Pyrimidines, and Mesenchymal Stem Cells. Behav Cogn Neurosci Rev. Jun. 2006;5 (2):63-79.
Lombardi et al., Systemic treatments with GM1 ganglioside reduce quinolinic acid-induced striatal lesions in the rat. Eur J Pharmacol. Dec. 12, 1989;174(1):123-125.
Maglione et al., Impaired Ganglioside Metabolism in Huntington's Disease and Neuroprotective Role of GM1. J Neurosci. Mar. 17, 2010;30(11):4072-4080.
Schengrund, Lipid rafts: Keys to neurodegeneration. Brain Res Bull. Apr. 29, 2010;82(1-2):7-17.
A Novel Gene Containing a Trinucleotide Repeat That is Expanded and Unstable on Huntington's Disease Chromosomes. The Huntington's Disease Collaborative Research Group . . . Cell Mar. 1993;72(6):971-983.
Abad-Rodriguez, Regulation of axonal development by plasma membrane gangliosides. J Neurochem Nov. 2007;103 Suppl 1:47-55.
Abe et al., Improved inhibitors of glucosylceramide synthase. J Biochem. Feb. 1992;111(2):191-196.
Alter, GM1 Ganglioside for Acute Ischemic Stroke. Trial Design Issues. Ann NY Acad Sci Jun. 19, 1998;845:391-401.
Anne et al., Phosphorylation of Huntingtin by Cyclin•Dependent Kinase 5 is Induced by DNA Damage and Regulates Wild-Type and Mutant Huntingtin Toxicity in Neurons. J Neurosci Jul. 4, 2007;27(27):7318-7328.
Bae et al., p. 53 Mediates Cellular Dysfunction and Behavioral Abnormalities in Huntington's Disease. Neuron Jul. 7, 2005;47(1):29-41.
Cattaneo and Conti, Generation and Characterization of Embryonic Striatal Conditionally Immortalized ST14A Cells. J Neurosci Res Jul. 15, 1998;53(2):223-234.
Chiavegatto et al., A Functional Role for Complex Gangliosides: Motor Deficits in GM2/GD2 Synthase Knockout Mice. Exp Neurol Dec. 2000;166(2):227-234.
Chinnock and Roberts, Gangliosides for acute spinal cord injury. Cochrane Database Syst Rev Apr. 18, 2005;(2): CD004444.
Cho et al., Induction of neostriatal neurogenesis slows disease progression in a transgenic murine model of Huntington disease. J Clin Invest. Oct. 2007;117(10):2889-2902.
Ciarmiello et al., Brain White-Matter Volume Loss and Glucose Hypometabolism Precede the Clinical Symptoms of Huntington's Disease. J Nucl Med. Feb. 2006;47(2):215-222.
Clarke et al., A one-hit model of cell death in inherited neuronal degenerations. Nature. Jul. 13, 2000;406 (6792):195-199.
Colin et al., Akt is altered in an animal model of Huntington's disease and in patients. Eur J Neurosci. Mar. 2005;21(6):1478-1488.
Copy of Non Final Office Action issued by the European Patent Office dated May 21, 2012 in PCT/CA2010001282.
Da Silva et al., Asymmetric membrane ganglioside sialidase activity specifies axonal fate. Nat Neurosci May 2005;8(5):606-615.
Desplats et al., Glycolipid and ganglioside metabolism imbalances in Huntington's disease. Neurobiol Dis Sep. 2007;27(3):265-277.
Duchemin et al., GM1-induced activation of phosphatidylinositol 3-kinase: involvement of Trk receptors. J Neurochem Mar. 2008;104(6):1466-1477.

(Continued)

*Primary Examiner* — Jonathan S Lau

(57) ABSTRACT

Huntington's disease (HD) is a neurodegenerative disorder caused by the expansion of a polyglutamine stretch in the protein huntingtin (Htt). HD neurons are dysfunctional at multiple levels and have increased susceptibility to stress and apoptotic stimuli. As described therein there is provided compound(s), composition(s), methods and/or kits for the treatment and/or diagnosis of Huntington's disease.

10 Claims, 20 Drawing Sheets

(56) References Cited

OTHER PUBLICATIONS

Dunah et al., Sp1 and TAFII130 Transcriptional Activity Disrupted in Early Huntington's Disease. Science Jun. 2002 21;296(5576)2238-2243.
Fan and Raymond, N-methyi-D-aspartate (NMDA) receptor function and excitotoxicity in Huntington's disease. Prog Neurobiol Apr. 2007;81(5-6):272-293.
Farr et al., Bilateral alteration in stepping pattern after unilateral motor cortex injury: a new test strategy for analysis of skilled limb movements in neurological mouse models. J Neurosci Methods May 15, 2006;153(1):104-113.
Favaron et al., Gangliosides prevent glutamate and kainate neurotoxicity in primary neuronal cultures of neonatal rat cerebellum and cortex. Proc Natl Acad Sci USA Oct. 1988;85(19):7351-7355.
Ferrante, Mouse models of Huntington's disease and methodological considerations for therapeutic trials. Biochim Biophys Acta Jun. 2009;1792(6):506-520.
Ferrari et al., Prevention of Apoptotic Neuronal Death by GM1 Ganglioside. Involvement of Trk neurotrophin receptors. J Biol Chem Feb. 17, 1995;270(7):3074-3080.
Fishman et al., Deficient Ganglioside Biosynthesis: A Novel Human Sphingolipidosis. Science Jan. 10, 1975;187(4171):68-70.
Furuse et al., Effect of the mono- and tetra-sialogangliosides, GM1 and GQ1b, on long-term potentiation in the CA1 hippocampal neurons of the guinea pig. Exp Brain Res Dec. 1998;123(3):307-314.
Gauthier et al., Huntingtin Controls Neurotrophic Support and Survival of Neurons by Enhancing BDNF Vesicular Transport Along Microtubules. Cell Jul. 9, 2004;118(1):127-138.
Graham et al., Cleavage at the Caspase-6 Site Is Required for Neuronal Dysfunction and Degeneration Due to Mutant Huntingtin. Cell Jun. 16, 2006;125(6):1179-1191.
Gu et al., Serines 13 and 16 Are Critical Determinants of Full-Length Human Mutant Huntingtin Induced Disease Pathogenesis in HD Mice. Neuron Dec. 24, 2009;64(6):828-840.
Hakomori, The glycosynapse. Proc Natl Acad Sci USA Jan. 8, 2002;99(1):225-232.
Hickey and Chesselet, Apoptosis in Huntington's disease. Prog Neuropsychopharmacol Biol Psychiatry Apr. 2003;27(2):255-265.
Holmgren et al., Interaction of cholera toxin and membrane GM1 ganglioside of small intestine. Proc Natl Acad Sci USA Jul. 1975;72(7):2520-2524.
Humbert et al., The IGF-1/Akt Pathway Is Neuroprotective in Huntington's Disease and Involves Huntingtin Phosphorylation by Akt. Dev Cell Jun. 2002;2(6):831-837.
Ichikawa et al., Binding of laminin-1 to monosialoganglioside GM1 in lipid rafts is crucial for neurite outgrowth. J Cell Sci Jan. 15, 2009:122(Pt 2):289-299.
Imarisio et al., Huntington's disease: from pathology and genetics to potential therapies. Biochem J Jun. 1, 2008;412(2):191-209.
Kaplan and Miller, Neurotrophin signal transduction in the nervous system. Curr Opin Neurobiol Jun. 2000;10(3):381-391.
Karten et al., Generation and function of astroglial lipoproteins from Niemann-Pick type C1- deficient mice. Biochem J May 1, 2005;387(Pt 3):779-788.
Ladisch and Gillard, A Solvent Partition Method for Microscale Ganglioside Purification. Anal Biochem Apr. 1985;146(1):220-231.
Ledeen and Wu, Nuclear sphingolipids: metabolism and signaling. J Lipid Res Jun. 2008; 49(6):1176-1186.
Ledeen and Yu, Gangliosides: Structure, Isolation, and Analysis. Methods Enzymol 1982;83:139-191.
Ledeen, Ganglioside Structures and Distribution: Are They Localized at the Nerve Ending? J Supramol Struct 1978;8(1):1-17.
Lievens et al., Expanded polyglutamine peptides disrupt EGF receptor signaling and glutamate transporter expression in Drosophila. Hum Mol Genet Mar. 1, 2005;14(5):713-724.
Liu et al., A genetic model of substrate deprivation therapy for a glycosphingolipid storage disorder. J Clin Invest Feb. 1999;103(4):497-505.
Lopez and Schnaar, Gangliosides in cell recognition and membrane protein regulation. Curr Opin Struct Biol Oct. 2009;19(5):549-557.
Luo et al., Cdk5 phosphorylation of huntingtin reduces its cleavage by caspases: implications for mutant huntingtin toxicity. J Cell Biol May 23, 2005;169(4)647-656.
Mangiarini et al., Exon 1 of the HD Gene with an Expanded CAG Repeat Is Sufficient to Cause a Progressive Neurological Phenotype in Transgenic Mice. Cell Nov. 1, 1996;87(3):493-506.
Max et al., GM3 (hematoside) sphingolipodystrophy. N Engl J Med Oct. 31, 1974;291(18):929-931.
Miyagi et al., Plasma Membrane-associated Sialidase as a Crucial Regulator of Transmembrane Signalling. J Biochem Sep. 2008;144(3):279-285.
Mocchetti, Exogenous gangliosides, neuronal plasticity and repair, and the neurotrophins. Cell Mol Life Sci Oct. 2005; 62(19-20):2283-2294.
Oblinger et al., Domain-Dependent Modulation of PDGFRbeta by Ganglioside GM1. J Mol Neurosci Apr. 2003;20(2):103-114.
Oppenheimer, GM1 Ganglioside Therapy in Acute Ischemic Stroke. Stroke May 1990;21(5):825.
Pardridge, Transnasal and intraventricular delivery in Peptide drug delivery to the brain. Raven Press, 1991: 112.
Pope-Coleman et al., Effects of GM1 Ganglioside Treatment on Pre- and Postsynaptic Dopaminergic Markers in the Striatum of Parkinsonian Monkeys. Synapse May 2000;36(2):120-128.
Pouladi et al., Prevention of depressive behaviour in the YAC128 mouse model of Huntington disease by mutation at residue 586 of huntingtin. Brain Apr. 2009;132(Pt 4):919-932.
Prinetti et al., Glycosphingolipid behaviour in complex membranes. Biochim Biophys Acta Jan. 2009;1788(1):184-193.
Rabin et al., Gangliosides Activate Trk Receptors by Inducing the Release of Neurotrophins. J Biol Chem Dec. 20, 2002;277(51):49466-49472.
Rangone et al., The serum- and glucocorticoid-induced kinase SGK inhibits mutant huntingtin-induced toxicity by phosphorylating serine 421 of huntingtin. Eur J Neurosci Jan. 2004;19(2):273-279.
Rigamonti et al., Huntingtin's Neuroprotective Activity Occurs via Inhibition of Procaspase-9 Processing. J Biol Chem May 4, 2001;276(18):14545-14548.
Saito et al., Gangliosides Attenuate Ethanol•Induced Apoptosis in Rat Cerebellar Granule Neurons. Neurochem Res Sep. 1999;24(9):1107-1115.
Schilling et al., Huntingtin Phosphorylation Sites Mapped by Mass Spectrometry. Modulation of Cleavage and Toxicity. J Biol Chem Aug. 18, 2006;281(33):23686-23697.
Schneider, GM1 Ganglioside in the Treatment of Parkinson's Disease. Ann N Y Acad Sci Jun. 19, 1998;845:363-373.
Sciannamblo et al., Changes of the ganglioside pattern and content in human fibroblasts by high density cell population subculture progression. Glycoconj J Mar. 2002; 19(3):181-186.
Seyfried and Yu, Ganglioside GD3: structure, cellular distribution, and possible function. Mol Cell Biochem Sep. 1985;68(1):3-10.
Sheikh et al., Mice lacking complex gangliosides develop Wallerian degeneration and myelination defects. Proc Natl Acad Sci USA Jun. 22, 1999;96(13):7532-7537.
Simpson et al., Infantile-onset symptomatic epilepsy syndrome caused by a homozygous loss-of-function mutation of GM3 synthase. Nat Genet Nov. 2004;36(11):1225-1229.
Singhrao et al., Huntingtin protein colocalizes with lesions of neurodegenerative diseases: An investigation in Huntington's, Alzheimer's, and Pick's diseases. Exp Neurol Apr. 1998;150(2):213-222.
Sipione et al., Early transcriptional profiles in huntingtin•inducible striatal cells by microarray analyses. Hum Mol Genet Aug. 15, 2002;11(17):1953-1965.
Slow et al., Selective striatal neuronal loss in a YAC128 mouse model of Huntington disease. Hum Mol Genet Jul. 1, 2003;12(13):1555-1567.
Song et al., Expression of Full-Length Polyglutamine•expanded Huntingtin Disrupts Growth Factor Receptor Signaling in Rat Pheochromocytoma (PC12) Cells. J Biol Chem Feb. 22, 2002;277(8):6703-6707.
Sonnino et al., Gangliosides as components of lipid membrane domains. Glycobiology Jan. 2007;17(1):1R-13R.

(56) References Cited

OTHER PUBLICATIONS

Squitieri et al., Juvenile Huntington's disease: Does a dosage-effect pathogenic mechanism differ from the classical adult disease? Mech Ageing Dev Feb. 2006;127(2):208-212.

Stine et al., Correlation between the onset age of Huntington's disease and length of the trinucleotide repeat in IT-15. Hum Mol Genet Oct. 1993;2(10):1547-1549.

Sun et al., Myelin-associated glycoprotein (Siglec-4) expression is progressively and selectively decreased in the brains of mice lacking complex gangliosides. Glycobiology Sep. 2004;14(9):851-857.

Svennerholm, Quantitative estimation of sialic acids. II. A colorimetric resorcinol-hydrochloric acid method. Biochim Biophys Acta Jun. 1957;24(3):604-611.

Tapley et al., K252a is a selective inhibitor of the tyrosine protein kinase activity of the trk family of oncogenes and neurotrophin receptors. Oncogene Feb. 1992;7(2):371-381.

Tettamanti et al., Sub•synaptosomal localization of brain particulate neuraminidase. Brain Res Dec. 12, 1972;47(2):515-518.

Tettamanti, Ganglioside/glycosphingolipid turnover: New concepts. Glycoconj J 2004;20(5):301-317.

Toledo et al., Effect of Ganglioside and Tetraspanins in Microdomains on Interaction of Integrins with Fibroblast Growth Factor Receptor. J Biol Chem Apr. 22, 2005;280(16):16227-16234.

Trettel et al., Dominant phenotypes produced by the HD mutation in STHdh(Q111) striatal cells. Hum Mol Genet Nov. 22, 2000;9(19):2799-2809.

Van Raamsdonk et al., Wild-type huntingtin ameliorates striatal neuronal atrophy but does not prevent other abnormalities in the YAC128 mouse model of Huntington disease. BMC Neurosci Dec. 5, 2006;7:80 (9pp).

Van Raamsdonk et al., Cognitive Dysfunction Precedes Neuropathology and Motor Abnormalities in the YAC128 Mouse Model of Huntington's Disease. J Neurosci Apr. 20, 2005;25(16)4169-4180.

Van Raamsdonk et al., Phenotypic abnormalities in the YAC128 mouse model of Huntington disease are penetrant on multiple genetic backgrounds and modulated by strain. Neurobiol Dis Apr. 2007;26(1):189-200.

Van Raamsdonk et al., Selective degeneration and nuclear localization of mutant huntingtin in the YAC128 mouse model of Huntington disease. Hum Mol Genet Dec. 15, 2005;14(24):3823-3835.

Vucic et al., Guillain-Barre syndrome: An update. J Clin Neurosci Jun. 2009;16(6):733-741.

Vyas et al., Gangliosides are functional nerve cell ligands for myelin•associated glycoprotein (MAG), an inhibitor of nerve regeneration. Proc Natl Acad Sci USA Jun. 11, 2002;99(12):8412-8417.

Wade et al., Atrophy and degeneration in sciatic nerve of presymptomatic mice carrying the Huntington's disease mutation. Brain Res Jan. 10, 2008;1188:61-68.

Walker, Huntington's disease. Lancet Jan. 20, 2007;369(9557):218-228.

Warby et al., Huntingtin phosphorylation on serine 421 is significantly reduced in the striatum and by polyglutamine expansion in vivo. Hum Mol Genet Jun. 1, 2005;14(11):1569-1577.

Warby et al., Phosphorylation of huntingtin reduces the accumulation of its nuclear fragments. Mol Cell Neurosci Feb. 2009;40(2):121-127.

Wieraszko and Seifert, The role of monosialoganglioside GM1 in the synaptic plasticity: in vitro study on rat hippocampal slices. Brain Res Oct. 14, 1985;345(1):159-164.

Wu et al., Cerebellar neurons lacking complex gangliosides degenerate in the presence of depolarizing levels of potassium. Proc Natl Acad Sci USA Jan. 2, 2001;98(1):307-312.

Wu et al., Enhanced Susceptibility to Kainate-Induced Seizures, Neuronal Apoptosis, and Death in Mice Lacking Gangliotetraose Gangliosides: Protection with LIGA 20, a Membrane-Permeant Analog of GM1. J Neurosci Nov. 23, 2005;25(47):11014-11022.

Wu et al., Induction of Calcium Influx through TRPC5 Channels by Cross-Linking of GM1 Ganglioside Associated with alpha5beta1 Integrin Initiates Neurite Outgrowth. J Neurosci Jul. 11, 2007;27(28):7447-7458.

Wu et al., Susceptibility of cerebellar granule neurons from GM2/GD2 synthase-null mice to apoptosis induced by glutamate excitotoxicity and elevated KCl: rescue by GM1 and LIGA20. Glycoconj J 2004;21(6):305-313.

Xia et al., Characterization of the promoter and the transcription factors for the mouse UDP-Gal:betaGlcNAc beta1,3-galactosyltransferase gene. Gene May 8, 2003;309(2):117-123.

Yang et al., Akt/Protein Kinase B Signaling Inhibitor-2, a Selective Small Molecule Inhibitor of Akt Signaling with Antitumor Activity in Cancer Cells Overexpressing Akt. Cancer Res Jul. 1, 2004;64(13):4394-4399.

Yoon et al., Epidermal growth factor receptor tyrosine kinase is modulated by GM3 interaction with N-linked GlcNAc termini of the receptor. Proc Natl Acad Sci USA Dec. 12, 2006;103(50):18987-18991.

Yu et al., Regulation of ganglioside biosynthesis in the nervous system. J Lipid Res May, 2004;45(5):783-793.

Yu et al., The role of glycosphingolipid metabolism in the developing brain. J Lipid Res Apr. 2009;50 Suppl:S440-445.

Zala et al., Phosphorylation of mutant huntingtin at S421 restores anterograde and retrograde transport in neurons. Hum Mol Genet Dec. 15, 2008;17(24):3837-3846.

Zuccato et al., Loss of Huntingtin-Mediated BDNF Gene Transcription in Huntington's Disease. Science Jul. 20, 2001;293(5529):493-498.

Ariga et al. Characterization of high-affinity binding between gangliosides and amyloid β-protein. Archives of Biochemistry and Biophysics, vol. 388, No. 2, pp. 225-230, Apr. 15, 2001.

Ariga et al. The pathological roles of ganglioside metabolism in Alzheimer's disease: effects of gangliosides on neurogenesis. International Journal of Alzheimer's Disease, vol. 2011, Article ID 193618, 14 pages, 2011.

Chi et al. Ganglioside GM1-Mediated amyloid-beta fibrillogenesis and membrane disruption. Biochemistry 2007, 46,1913-1924.

Crook et al. Huntington's Disease: can mice lead the way to treatment? Neuron 69, Feb. 10, 2011, pp. 423-435.

Cubo et al. Effect of donepezil on motor and cognitive function in Huntington disease. Neurology 2006;67;1268-1271.

Denny et al. Cerebellar lipid differences between R6/1 transgenis mice and humans with Huntington's disease. Journal of Neurochemistry (2010) 115, 748-758.

Hayashi et al. A seed for Alzheimer amyloid in the brain. The Journal of Neuroscience, May 19, 2004, 24(20);4894-4902.

The Huntington'S Disease Collaborative Research Group—A novel gene containing a trinucleotide repeat that is expanded and unstable on Huntington's disease chromosomes. Cell, Vo. 72, 971-983, Mar. 16, 1993.

Imarisio et al. Huntington's disease: from pathology and genetics to potential therapies. Biochem. J. (2008)412, 191-209.

Jauhar et al. Psychiatric and behavioural manifestations of Huntington's disease. APT 2010, 16:168-175.

Kabio et al. Interaction of amyloid β-protein with various gangliosides in raft-like membranes: importance of GM1 ganglioside-bound form as an endogenous seed for Alzheimer amyloid. Biochemistry 2002, 41, 7385-7390.

Menalled et al. Mouse models of Huntington's disease. Trends in Pharmacological Sciences, vol. 23, No. 1, Jan. 2002, pp. 32-39.

Molander-Melin et al. Structural membrane alterations in Alzheimer brains found to be associated with regional disease development; increased density of gangliosides GM1 and GM2 and loss . . . Journal of Neurochemistry, 2005, 92, 171-182.

Mott et al. Neuropathology of Alzheimer's disease. Neuroimaging Clinics of Norrth America 15 (2005) 755-765.

Nilsberth et al. The arctic APP mutation (E693G) causes Alzheimer's disease by enhanced Aβprotofibril formation. Nature Neuroscience, vol. 4, No. 9, Sep. 2001, pp. 887-893.

Perl, Daniel P. Neuropathology of Alzheimer's disease. Mount Sinai Journal of Medicine 77:32-43, 2010.

(56) References Cited

OTHER PUBLICATIONS

Ramaswamy et al. Animal models of Huntington's disease. ILAR Journal, vol. 48, No. 4, pp. 356-373, 2007.

Svennerholm et al. Membranes lipids, selectively diminished in Alzheimer brains, suggest synapse loss as a primary event in early-onset form (type I) and demyelination in late-onset form (typt II). Journal of Neurochemistry, vol. 62, No. 3, pp. 1039-1047, 1994.

Yamamoto et al. Accelerated Aβ aggregation in the presence of GM1-ganglioside-accumulated synaptosomes of aged apoE4-knock-in mouse brain. FEBS Letters 569 (2004) 135-139.

Yamamoto et al. A ganglioside-induced toxic soluble Aβ assembly: its enhanced formation from Aβbearing the arctic mutation. The Journal of Biological Chemistry, 2007, 282:2646-2655.

Yanagisawa et al. GM1 ganglioside-bound amyloid β-protein (Aβ): a possible form of preamyloid in Alzheimer's disease. Nature Medicine, vol. 1, No. 10, pp. 1062-1066, Oct. 1995.

Yanagisawa et al. GM1 ganglioside and the seeding of amyloid in Alzheimer's disease: endogenous seed for Alzheimer amyloid. The Neuroscientist 2005, 11:250-260.

Yang et al. Mouse models for validating preclinical candidates for Huntington's disease. Neurobiology of Huntington's Disease NCBI Bookshelf, 2011.

Zha et al. GM1 ganglioside regulates the proteolysis of amyloid precursor protein. Molecular Psychiatry (2004) 9, 946-952.

Zuccato et al. Molecular mechanisms and potential therapeutic targets in Huntington's disease. Physiol Rev 90: 905-981, 2010.

\* cited by examiner

FIGURE 5
A
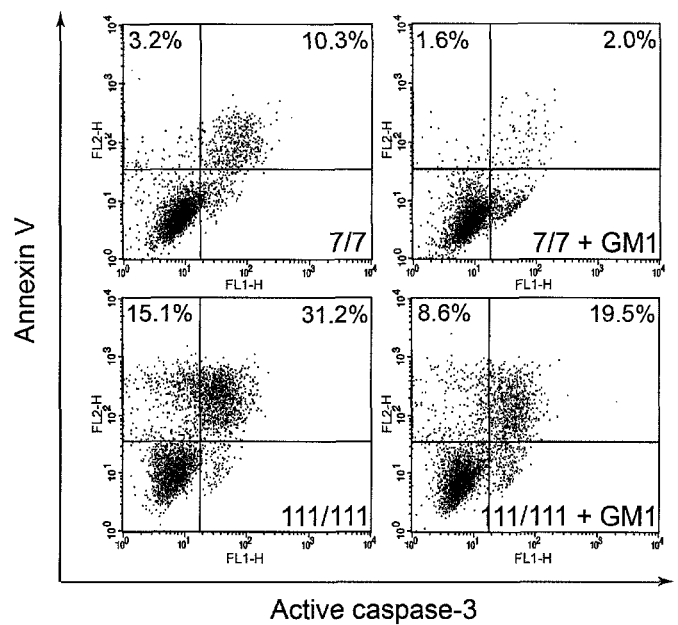
B
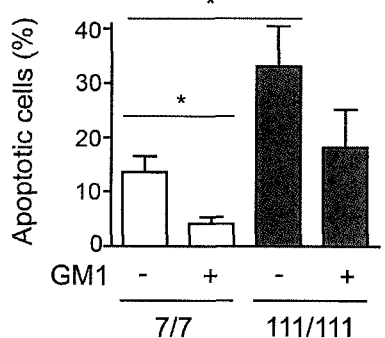
C
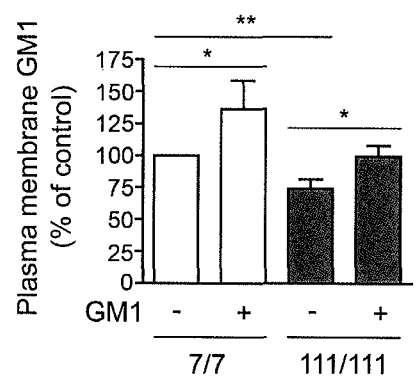

Figure 11

| Patient I.D. | Age at biopsy (yrs) | Gender | (CAG)n | Age of onset |
|---|---|---|---|---|
| C1 (control) | 36 | Male | Normal | N/A |
| C2 (control) | 15 | Male | Normal | N/A |
| HD45 | 35 | Male | 21/45 | unknown |
| HD50 | 11 | Male | 20/50 | 26 years |
| HD61 | 29 | Female | 20/61 | 18 years |
| HD86 | 10 | Male | 22/86 | 2 years |

FIGURE 12

| GeneBank Accession # | Gene Name | Mouse Sequence | |
|---|---|---|---|
| NM_011673 | Ugcg | Fwd<br>Rev | 5' TTG TTC GGC TTC GTG CTC TT 3'<br>5' GAG ACA CCA GGG AGC TTG CT 3' |
| NM_011375 | St3gal5 | Fwd<br>Rev | 5' ATA TGC TGC CCG AAC ATG ACT 3'<br>5' CAA CTG GCG CAC TGT TCA AC 3' |
| NM_008080 | B4galnt1 | Fwd<br>Rev | 5' CCA GCC CAG TTC TGG ATA AAC T 3'<br>5' GGT TGG GAG GGT GTC TTA CGA 3' |
| NM_019420 | B3galt4 | Fwd<br>Rev | 5' GGC AGT GCC CCT TCT GTA TTT 3'<br>5' CGA GGC ATA GGG TGG AAA AG 3' |
| NM_009179 | St3gal2 | Fwd<br>Rev | 5' CAC CCT GAC TCG GCT GCT T 3'<br>5' TCT CGC GCC TTA GGG CTA A 3' |
| NM_011374 | St8sia1 | Fwd<br>Rev | 5' TCC AGC TGC CAT TGA AGA AA 3'<br>5' TGG ACC CGA CAT CTC TGG TGT A 3' |
| NM_009182 | St8sia3 | Fwd<br>Rev | 5' CCA GTC ATT TGT GCC CAT TAC 3'<br>5' GGG ACC GGA AGT TAT TGC TA 3' |
| NM_008907 | Cyp A | Fwd<br>Rev | 5' TCC AAA GAC AGC AGA AAA CTT TCG 3'<br>5' TCT TCT TGC TGG TCT TGC CAT TCC 3' |

| GeneBank Accession # | Gene Name | Human Sequence | |
|---|---|---|---|
| NM_003782 | B3GALT4 | Fwd<br>Rev | 5' GGC CCG ATA CGT CCT CAA G 3'<br>5' CAA AAC CTG GCC TCC TTC CT 3' |
| NM_021130 | CYP A | Fwd<br>Rev | 5' CCC ATT TGC TCG CAG TAT CC 3'<br>5' GGA AAA CAT GGA ACC CAA AGG 3' |

FIGURE 13
Liga20 is not protective in a genetic cell model of HD
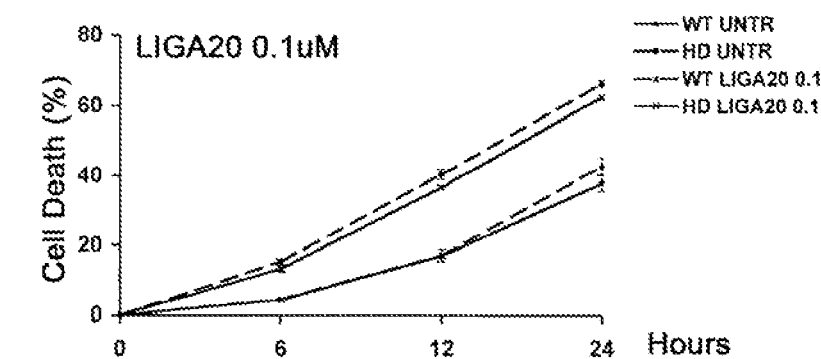
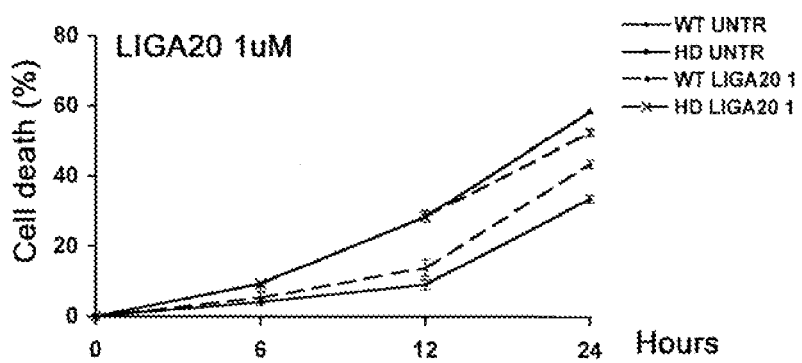
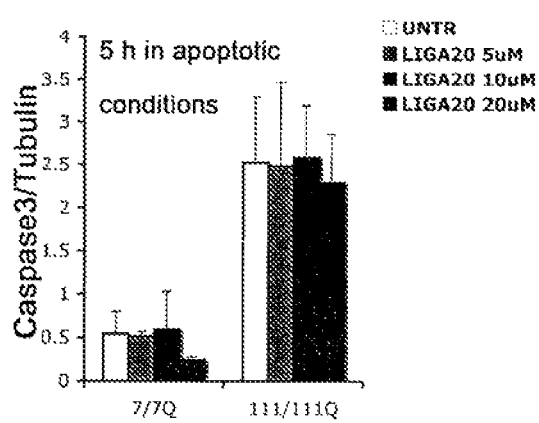

Figure 18
A.
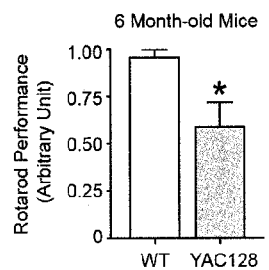
B.
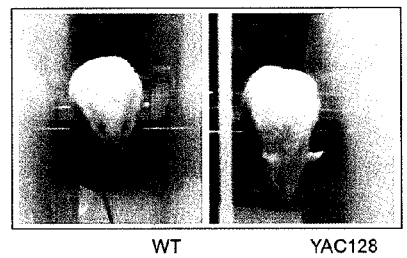
C.
Ladder Rung Task
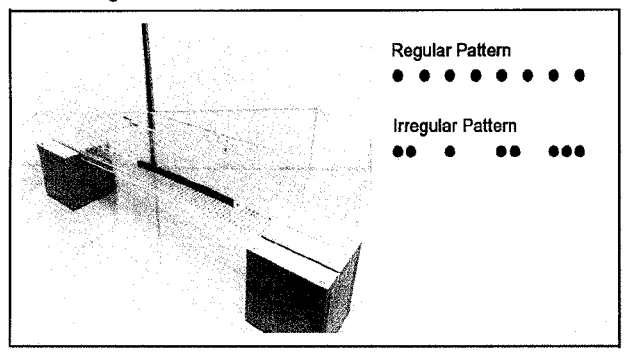
D.
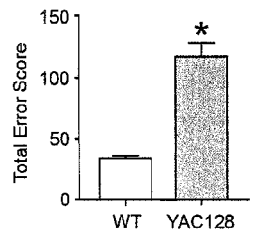

FIGURE 19
A.
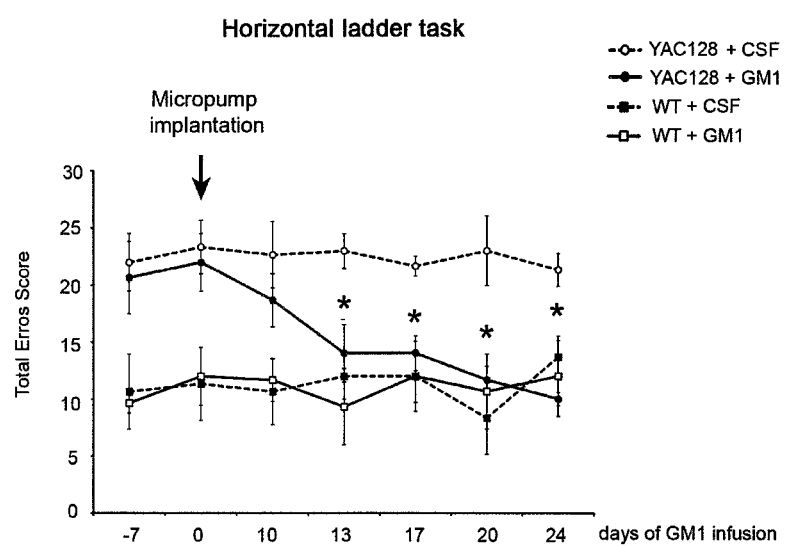
B.
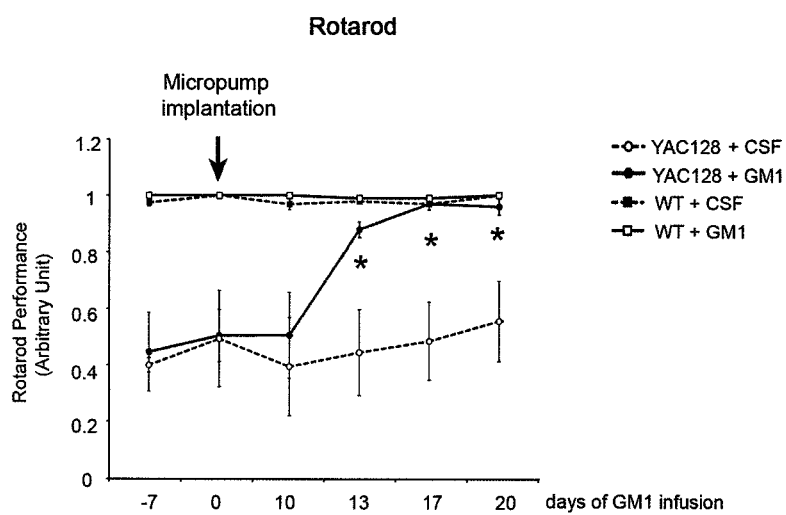

ns and claims.

NEUROPROTECTIVE GANGLIOSIDE COMPOSITIONS FOR USE IN TREATING HUNTINGTON'S DISEASE

RELATED APPLICATIONS

The present invention is filed under 35 U.S.C. §371 as the U.S. national phase of International Application No. PCT/CA2010/001282, filed Aug. 20, 2010, which designated the U.S. and claims the benefit of priority to U.S. Provisional Application No. 61/239,953 filed Sep. 4, 2009, which is hereby incorporated in its entirety including all tables, figures and claims.

FIELD OF THE INVENTION

The field of the invention generally relates to compounds, compositions, methods and/or kits for treating and/or diagnosing Huntington's disease.

BACKGROUND OF THE INVENTION

Huntington's disease (HD) is the most common inherited neurodegenerative disorder and is characterized by chorea and progressive motor, psychiatric and cognitive decline (Walker, 2007). The disease is caused by a mutation in the HD gene which encodes huntingtin (Htt) (Cell(1993)26; 72(6): 971-83), a ubiquitous protein with still unclear function. The HD gene contains a polymorphic CAG trinucleotide repeat that is translated as a stretch of glutamines (polyQ) in the N-terminal of the protein. Up to 35 CAG repeats are present in healthy individuals, whereas 36 or more repeats determine HD pathology. The higher the number of CAG repeats, the earlier is disease onset (Stine et al., 1993). To date there is no cure for HD, as the mechanisms underlying the disease are still poorly understood.

Neurodegeneration in HD is likely the result of a domino effect that is triggered by mutant Htt (mHtt). Expansion of the polyQ stretch endows the mutant protein with toxic properties. As a result, neurons expressing mHtt develop a broad array of cell dysfunctions, including transcriptional dysregulation, mitochondrial metabolism aberrations, and impaired cell signaling, axonal transport and synaptic activity (Imarisio et al., 2008). HD cells are also more susceptible to apoptotic stimuli than normal cells (Hickey and Chesselet, 2003). Neurons bearing the mutation are thought to be in an abnormal homeostatic state characterized by lower thresholds for the activation of cell death (Clarke et al., 2000). This may be, at least in part, the result of impaired cell signaling and overall imbalance between activation of pro-survival and apoptotic pathways. In fact, the p53 pathway, an important player in the cell response to a variety of stressors, is upregulated in HD neurons (Bae et al., 2005; Sipione et al., 2002). On the other hand, activation of the PI3K/AKT pathway, the major pro-survival pathway in neurons (Kaplan and Miller, 2000), is impaired in HD models and patients' lymphocytes (Colin et al., 2005; Humbert et al., 2002; Song et al., 2002). The mechanism behind these dysfunctions has not been identified yet, but a role for mHtt in the regulation of growth factor receptors activity and downstream signaling has been proposed (Lievens et al., 2005; Song et al., 2002).

Generation of toxic N-terminal fragments of mHtt by proteolytic cleavage of the full-length protein represents a critical step in the development of neural dysfunction and HD pathogenesis (Graham et al., 2006; Imarisio et al., 2008). Protein cleavage and toxicity may be decreased by phosphorylation of mHtt by AKT (Humbert et al., 2002; Warby et al., 2009) and other kinases (Anne et al., 2007; Luo et al., 2005; Rangone et al., 2004; Schilling et al., 2006).

Gangliosides are sialic acid-containing glycosphingolipids that are particularly enriched in the brain, where they contribute up to 10% of the neuronal lipid content (Ledeen, 1978). Together with cholesterol and sphingomyelin, gangliosides are major components of lipid rafts—membrane microdomains involved in cell signaling—and exert important cell regulatory functions (Sonnino et al., 2007). They play a major role in cell adhesion and cell-cell interaction (Hakomori Si, 2002) and mediate communication between axons and myelin in the central nervous system (CNS) (Vyas et al., 2002). They also modulate the activity of many tyrosine kinase receptors, including EGF receptor (Yoon et al., 2006), PDGF receptor (Oblinger et al., 2003), FGF receptor (Toledo et al., 2005) and neurotrophin receptors (Ferrari et al., 1995; Mocchetti, 2005).

There remains a need, therefore, for compounds, compositions, methods and/or kits for treating and/or diagnosing neurodegenerative, and for example Huntington's disease.

This background information is provided for the purpose of making known information believed by the applicant to be of possible relevance to the present invention. No admission is necessarily intended, nor should it be construed, that any of the preceding information constitutes prior art against the present invention.

SUMMARY OF THE INVENTION

An object of the present invention is to provide a compounds, compositions, methods and/or kits for treating and/or diagnosing Huntington's disease.

In accordance with one aspect of the present invention, there is provided a method comprising: a) obtaining a sample from a subject, b) contacting the sample with cholera toxin B to form a complex between the cholera toxin B and GM1 in the sample; c) measuring and/or detecting the complex formed to determine an amount of GM1 in the sample; d) determining the onset and/or development of Huntington's disease, wherein the onset and/or development of Huntington's disease is indicated by the level of GM1 in the sample.

In accordance with another aspect of the present invention, there is provided a method comprising: a) obtaining a sample from a subject, b) analyzing the sample and optionally a control using a confocal microscope, a flow cytometer, in cell western assay, ELISA, or dot-blotting having a detector set to detect a complex formed between cholera toxin B and GM1 within the sample; and c) determining the onset and/or development of Huntington's disease, wherein the onset and/or development of Huntington's disease is indicated by the level of GM1 in the sample.

In accordance with one aspect of the present invention, there is provided a method comprising: a) obtaining a sample from a subject, b) contacting the sample with an antibody direct to GM1 to form a complex between the antibody and GM1 in the sample; c) measuring and/or detecting the complex formed to determine an amount of GM1 in the sample; d) determining the onset and/or development of Huntington's disease, wherein the onset and/or development of Huntington's disease is indicated by the level of GM1 in the sample.

In accordance with another aspect of the present invention, there is provided a method comprising: a) obtaining a sample from a subject, b) analyzing the sample and optionally a control using a confocal microscope, a flow cytometer, in cell western assay, ELISA or dot-blotting having a detector set to detect a complex formed between an antibody direct to GM1 and GM1 within the sample; and c) determining the onset and/or development of Huntington's disease, wherein the onset and/or development of Huntington's disease is indicated by the level of GM1 in the sample.

In accordance with another aspect of the present invention, there is provided a method comprising: a) obtaining a sample from a subject, b) analyzing the sample using thin layer chromatography and c) determining the onset and/or development of Huntington's disease, wherein the onset and/or development of Huntington's disease is indicated by the level of GM1 in the sample.

In accordance with one aspect of the present invention, there is provided a method comprising: a) obtaining a sample from a subject, b) measuring and/or detecting the amount of B3GalT4 mRNA in said sample; d) determining the onset and/or development of Huntington's disease, wherein the onset and/or development of Huntington's disease is indicated by the level of B3GalT4 mRNA in the sample.

In another aspect of the present invention, there is provided a method comprising: a) obtaining a sample from a subject; and b) analyzing the sample to identify GM1, wherein the onset and/or development of Huntington's disease in the subject is indicated by the level of GM1 in the sample.

In another aspect of the present invention, there is provided a method comprising, administering to a subject for the treatment of Huntington's disease an effective therapeutic amount of GM1.

In another aspect of the present invention, there is provided a method comprising, administering to a subject for the treatment of Huntington's disease an effective therapeutic amount of GM3.

In another aspect of the present invention, there is provided a method comprising, administering to a subject for the treatment of Huntington's disease an effective therapeutic amount of GM1, wherein the GM1 administered results in (i) increased levels of GM1 in the HD cells in the subject or (ii) reduces the susceptibility of the HD cells in the subject to apoptosis as compared to untreated HD cells or (iii) results in increased phosphorylation of mHtt in HD cells in the subject, or (vi) combinations thereof.

In another aspect of the present invention, there is provided a use of GM1 in the manufacture of a medicament suitable for the treatment of Huntington's disease.

In another aspect of the present invention, there is provided a use of GM1 suitable for the treatment of Huntington's disease.

In another aspect of the present invention, there is provided a use of GM1 for protecting HD cells from apoptosis.

In another aspect of the present invention, there is provided a use of GM3 in the manufacture of a medicament suitable for the treatment of Huntington's disease.

In another aspect of the present invention, there is provided a use of GM3 suitable for the treatment of Huntington's disease.

In another aspect of the present invention, there is provided a use of GM3 for protecting HD cells from apoptosis.

In accordance with another aspect of the present invention there is provided a kit for determining the onset and/or development of Huntington's disease in a subject, comprising: a) instructions for determining an amount of GM1 in a sample from the subject; and b) a reagent for measuring the amount of GM1 in said sample. In a specific aspect, said reagent comprises cholera toxin B.

In accordance with another aspect of the present invention there is provided a kit for determining the onset and/or development of Huntington's disease in a subject, comprising: a) instructions for determining an amount of GM1 in a sample from the subject; and b) a reagent for measuring the amount of GM1 in said sample. In a specific aspect, said reagent comprises an antibody specific for GM1.

In accordance with another aspect of the present invention there is provided a kit for determining the onset and/or development of Huntington's disease in a subject, comprising: a) instructions for determining an amount of GD1a in a sample from the subject; and b) a reagent for measuring the amount of GD1a in said sample. In a specific aspect, said reagent comprises an antibody specific for GD1a.

In accordance with another aspect of the present invention there is provided a kit for determining the onset and/or development of Huntington's disease in a subject, comprising: a) instructions for determining an amount of GT1b in a sample from the subject; and b) a reagent for measuring the amount of GT1b in said sample. In a specific aspect, said reagent comprises an antibody specific for GT1b.

In accordance with another aspect of the present invention, there is provided a kit for determining the onset and development of Huntington's disease in a subject, comprising: a) instructions for determining an amount of B3GalT4 mRNA in a sample from the subject, and b) a reagent for measuring the amount of B3GalT4 mRNA in said sample. In a specific aspect, said reagent comprises reagents suitable for use in real-time or quantitative PCR, or northern blotting.

BRIEF DESCRIPTION OF THE DRAWINGS

Embodiments of the present invention will now be described, by way of example only, with reference to the attached Figures, wherein:

FIG. 12—Genes of the ganglioside biosynthetic pathway analyzed by qPCR and sequence of primers used in the analysis.

FIG. 13—Liga20 is not protective in a genetic cell model of HD. Immortalized knock-in striatal cells expressing wild-type (WT) or mutant (HD) huntingtin were exposed to apoptotic conditions for the indicated time in the absence or in the presence of the indicated concentrations of Liga20 (0.1-1-5-10-20 μM). Analysis of cell death was performed by annexinV binding and FACS analysis. Analysis of Caspase 3 activation, an another marker of apoptosis, was performed by in-cell western (Licor Odyssey), using anti-active caspase 3 antibodies. Data were normalized over tubulin.

FIG. 18—Analysis of motor behavior in YAC128 mice prior to GM1 infusion. Rotarod performance in impaired in YAC128 mice. (Panel A) Five-month old YAC128 and WT littermates underwent 3 sessions/day (60 seconds. each at 32 rpm) for 3 days. The graph represents the average performance of 6 mice per genotype over 3 days of training. (Panel B) Motor deficit in 6-month old YAC128 mice is also evident from their position on the rotarod. The horizontal ladder task is a sensitive measure of motor deficit in YAC128 mice. (Panel C) The horizontal ladder is made of metal rungs the pattern of which can be changed to increase task difficulty. Irregular patterns prevent the animal to learn the position of the rungs and highlight specific motor deficits. (Panel D) Six month-old YAC128 mice make more mistakes (deep and slight slips, total misses) than wild-type mice;

FIG. 19—GM1 infusion restores normal motor behavior in YAC128 mice. (Panel A) YAC128 and WT littermates infused with CSF or GM1 performed the horizontal ladder task for 3 days, starting at the indicated time after micropump implantation. The graph represents the average performance of 3 mice per group over 3 days of tests. *, $p<0.05$ (relative to YAC128 receiving CSF only). (Panel B) YAC128 and WT littermates infused with CSF or GM1 underwent 3 sessions/day (60 sec. each at 32 rpm) for 3 days, starting at the indicated time after micropump implantation. The graph represents the average performance of 3 mice per group over 3 days of training. *, $p<0.05$ (relative to YAC128 receiving CSF only).

Figure 1:
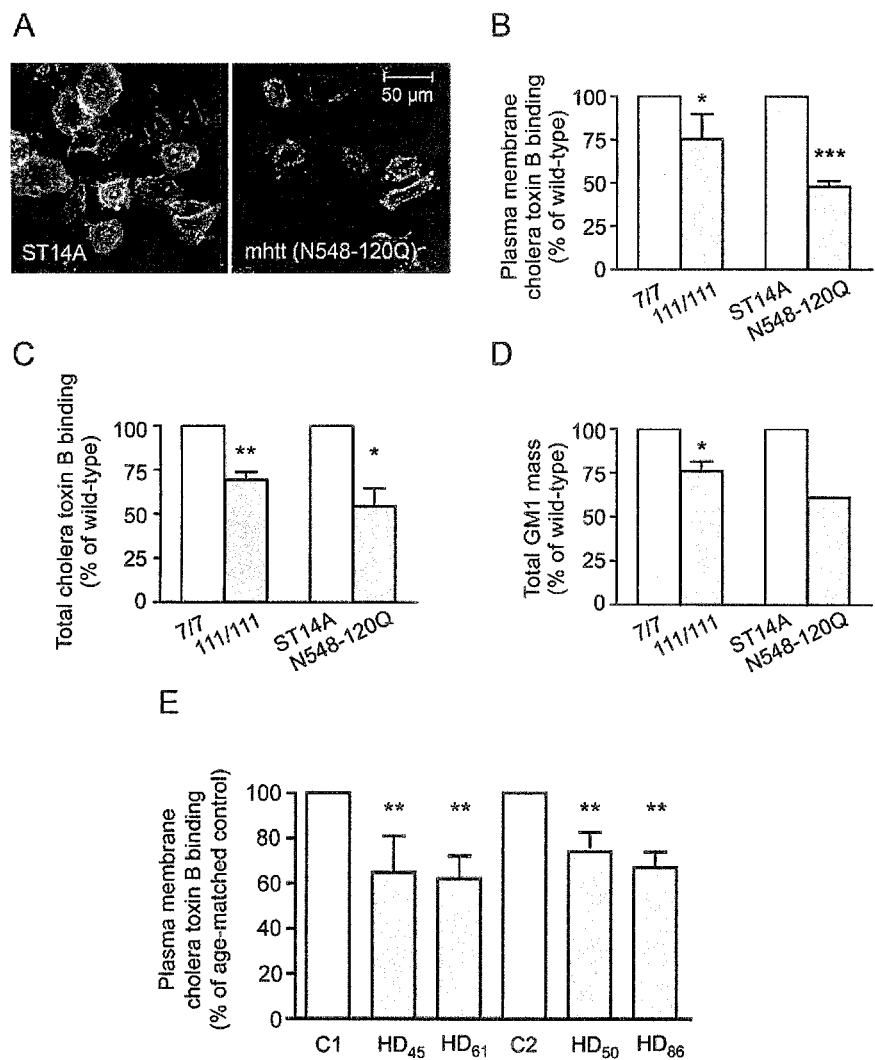
FIG. 1—Levels of the ganglioside GM1 are reduced in HD cells. A) Confocal microscopy images of parental (ST14A) and mHtt-expressing cells (N548-120Q) labeled with Alexa594-conjugated cholera toxin B at 4° C. to visualize plasma membrane GM1. Images are 3-dimensional reconstruction of confocal Z-stacks. B) Quantitation of plasma membrane GM1 by Alexa488-conjugated cholera toxin B labeling and FACS analysis. Data represent the mean±SD of 3-5 independent experiments, each performed in triplicates. C) Total (plasma membrane+intracellular) GM1 measured by cholera toxin B labeling of fixed and permeabilized cells. Data are the mean±SD of 3 experiments. D) Total GM1 measured in cell gangliosides extracts separated and visualized on TLC as described in Materials and Methods. E) Plasma membrane GM1 levels in human fibroblasts from HD patients and normal subjects. HD fibroblasts were compared to age-matched controls at the same passage number (C1 and C2). Subscripts represent the number of CAG repeats in the HD gene of the affected individuals. Additional information on human fibroblast lines is provided in FIG. 11 the mean±SD of three experiments performed on cells at three different passages in culture. 7/7, STHdh$^{7/7}$; 111/111, STHdh$^{111/111}$; *, $p<0.05$; , $p<0.001$; *, $p<0.0001$ FIG. 2—Expression of B3galt4 (GM1/GD1b synthase) is down-regulated in a striatal cell model of HD and in fibroblasts from HD patients. Gene expression analysis by quantitative real-time PCR in striatal knock-in cells (A) and in human fibroblasts (B). Data were normalized to cyclophilin A expression. HD fibroblasts were compared to age-matched controls at the same passage number (C1 and C2). Subscripts represent the number of CAG repeats in the HD gene of the affected individuals. Additional information on the human fibroblast lines is provided in FIG. 11. Data are the mean±SD of 2-4 independent experiments. 7/7, STHdh$^{7/7}$; 111/111, STHdh$^{111/111}$, $p<0.05$; , $p<0.001$; *, $p<0.0001$ FIG. 3—GM1 is reduced in striatum, cortex and neurons of YAC128 mice. A) Representative thin-layer chromatography (TLC) analysis of striatal and cortical gangliosides. Ganglioside standards (STDS) are indicated. B) Densitometric analysis of individual gangliosides extracted from brain regions of 6 YAC128 mice, separated by TLC and compared to 6 wild-type littermates. Each dot represents one individual YAC128 mouse. Data are expressed as ratios of HD over wild-type control. C) Total GM1 levels in primary cultures of neurons and astrocytes were measured by dot-blotting with HRP-conjugated cholera toxin B. Individual neural cultures from 12 YAC128 newborn mice and 12 wild-type littermates were analyzed. Astrocyte cultures from 16 YAC128 and 18 wild-type littermates were used. Data are expressed as mean percentage of the average of wild-type values SD. *, $p<0.05$; **, $p<0.001$.

In the Detailed Description that follows, the numbers in bold face type serve to identify the component parts that are described and referred to in relation to the drawings depicting various embodiments of the invention. It should be noted that in describing various embodiments of the present invention, the same reference numerals have been used to identify the same of similar elements. Moreover, for the sake of simplicity, part have been omitted from some figures of the drawings.

DETAILED DESCRIPTION

As will be described in more detail below, the present invention relates to compounds, compositions, methods, kits and/or the like, for treatment and/or diagnosis of Huntington's disease (HD) in a subject.

The term "subject", as used herein, refers to any animal who would benefit from treatment and/or diagnosis. Non-limiting examples of a subject includes humans, non-human primates, monkeys, mice, cultured cell lines and primary cell lines. In a specific example, the subject is a human.

The term "treatment" or "treating", as used herein, refers to preventing, reducing, ameliorating, abrogating, delaying disease progression, delaying disease onset, and/or the diminishment of pain. Treatment or treating may further comprise increasing the survival time of a subject suffering from HD, or increasing the survival time of an individual susceptible to HD. Delaying disease progression may be indicated by a lack of measurable change in, or an improvement of, one or more indicators of HD, including molecular markers or symptoms of the disease. An improvement in an indicator of HD may include the absence of an undesirable change, or the presence of a desirable change. Treatment or treating may refer to the reduction and/or improvement of any one of the overt symptoms of HD, including, but not limited to, psychiatric, cognitive or physical motor impairments. Non-limiting symptoms of HD include dementia or psychiatric disturbances, ranging from apathy and irritability to bipolar or schizophreniform disorder, physical motor impairment including chorea, hypokinesia, cognitive impairment, motor manifestations including flicking movements of the extremities, a lilting gait, motor impersistence, facial grimicing, ataxia and/or dystonia. It is to be understood that any clinically beneficial effect that arises from the methods, compounds, compositions and kits disclosed herein, is to be considered to be encompassed by the invention.

As used herein, "a subject suffering from HD" refers to a subject who has HD. In one example, a subject who has HD received a diagnosis of HD from, for example, a health profession professional, such as a physician. Relevant diagnostic tests are know in the art and include, but are not limited to, genetic testing to determine the presence of a mutation in the huntingtin gene, neurological examination, and brain imaging.

As used herein, "a subject susceptible to HD" refers to a subject who, hased on genetic testing and/or family history, is likely to develop HD.

One aspect of the present invention relates to the treatment of Huntington's disease in a human subject, said treatment comprises the administration of a therapeutically effective amount of a pharmaceutical composition comprising GM1.

Another aspect of the present invention relates to the treatment of Huntington's disease in a human subject, said treatment comprising the administration of a therapeutically effective amount of a pharmaceutical composition comprising GM3.

Another aspect of the present invention relates to the treatment of Huntington's disease in a human subject, said treatment comprising the administration of a therapeutically effective amount of a pharmaceutical composition comprising GD1a.

Another aspect of the present invention relates to the treatment of Huntington's disease in a human subject, said treatment comprising the administration of a therapeutically effective amount of a pharmaceutical composition comprising GD1b.

Another aspect of the present invention relates to the treatment of Huntington's disease in a human subject, said treatment comprising the administration of a therapeutically effective amount of a pharmaceutical composition comprising GT1b.

Methods of administration of the compounds and compositions of the present application include, but are not limited to, intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal, vaginal and intestinal mucosa, etc.). Administration may be endoscopic or sublingual/buccal. Administration and may be administered together with other biologically active agents. Administration can be systemic or local.

As used herein, "oral administration" includes administering the constituents of the combined preparation in a suitable oral form such as, e.g., tablets, capsules, suspensions, solutions or emulsions, powders, syrups, granules, and the like.

In a specific example, the compounds or compositions of the present application are administered by intraperitoneal administration. In another specific example, the compounds or compositions of the present application are administered by intramuscular administration. In a specific example, the compounds or compositions of the present application are administered by subcutaneous administration.

In another example, pulmonary administration is used, for example, by use of an inhaler or nebulizer, and formulation with an aerosolizing agent, by inhalation or insufflation of powders or aerosols, including by nebulizer (intratracheal, intranasal, epidermal and transdermal).

The pharmaceutical compounds or compositions of the invention may be administered into the central nervous system by any suitable route.

The pharmaceutical compositions and formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

In a specific example, treatment comprises administration of a therapeutically effective amount of a pharmaceutical composition comprising GM1 to the central nervous system (CNS) of a subject.

In a specific example, treatment provides GM1 to the tissues of the CNS by administration directly into the cerebrospinal fluid (CSF). Means of delivery to the CSF and brain include, but are not limited to intrathecal (IT), intracerebroventricular (ICV), and intraparenchymal administration. IT or ICV administration may be achieved through the use of surgically implanted pumps that infuse the therapeutic agent into the cerebrospinal fluid.

Intraparenchymal delivery may be achieved by the surgical placement of a catheter into the brain. As used herein, "delivery to the CSF" and "administration to the CSF" encompass the IT infusion or ICV infusion of GM1 through the use of an infusion pump. In some embodiments, IT infusion is a suitable means for delivery to the CSF. In other embodiments, GM1 is continuously infused into the CSF for the entire course of treatment; such administration is referred to as "continuous infusion" or, in the case of IT infusion, "continuous IT infusion." Also contemplated is continuous intraparenchymal infusion using a pump.

In some embodiments, an infusion pump is employed to deliver GM1 to the CNS. Such infusion pumps and their method of implantation and use are known to the skilled worker. In a specific example, the Medtronic SyncroMed® II pump, is employed to deliver GM1 to the CNS. The SyncroMed® II pump is surgically implanted according the procedures set forth by the manufacturer. The pump contains a reservoir for retaining a drug solution, which is pumped at a programmed dose into a catheter that is surgically implanted.

For intrathecal administration of a drug, the catheter is surgically intrathecally implanted. In the context of the methods provided herein, the drug is the pharmaceutical composition comprising GM1.

As used herein, "therapeutically effective amount" refers to an amount that provides a therapeutic benefit in the treatment, prevention or management of HD or an overt symptom of the disease. The therapeutically effective amount may vary depending upon age, sex, weight, symptoms and other factors. Certain factors may influence the dosage required to effectively treat a subject, including but not limited to the severity of the disease, previous treatments, the general health and/or age of the subject, and other diseases (if any) present. Treatment of a subject with a therapeutically effective amount of GM1 can include a single treatment or more than one treatment.

As used herein, "pharmaceutical composition" comprises a pharmacologically effective amount of GM1 and a pharmaceutically acceptable carrier.

As used herein, "pharmaceutically acceptable carrier" refers to a diluent or carrier for administration of GM1. Acceptable diluents and carriers are well known to the skilled worker. Selection of a diluent or carrier is based on a number of factors, including but not limited to, the solubility of the compound and the route of administration. Such considerations are well understood by the skilled worker. In one example, such carriers include, but are not limited to, saline, buffered saline, dextrose, water, glycerol, ethanol, and combinations thereof.

Compound(s)/Compositions(s)

The compound(s)/composition(s) of the present invention protects cells from apoptosis.

In one example of the present invention, administration of GM1 protects wild-type cells and HD cells from apoptosis. In another example, administration of GM1 restores susceptibility of HD to apoptosis to that of wild-type levels.

In another example, administration of GM1 to wild type cells further increases GM1 content in the cells, thereby further augmenting cells survival.

In yet another example, administration of GM1 abolished 1-phenyl-2-palmitoylamino-3-morpholino-1-propanol (PPMP)-induced susceptibility of cells to apoptosis.

In another example, administration of GM1 to cells increased the phospho-AKT/AKT ratio within the cells.

In another example, administration of GM1 to cells increases the level of phosphorylation of mHtt within the cells.

In one example, GM1 administration restores, partially or fully, cellular function(s) that is/are compromised and/or otherwise abnormal in HD. In one example, GM1 administration restores susceptibility to apoptosis.

In one example of the present invention, administration of GM3 protects wild-type cells and HD cells from apoptosis. In another example, administration of GM3 restores susceptibility of HD to apoptosis to that of wild-type levels.

In one example of the present invention, levels of GD1a and GT1b are decreased in samples obtained from HD (YAC128) mice.

In one example, administration of GM1 is carried out in vitro, including, but not limited to, in cultured cells. In a specific example, GM1 is administered to striatal neural progenitor cells. In another specific example the striatal neural progenitor cell line is STHhd7/7 and STHhd111/111.

Method(s)

In one aspect of the present invention, there is provided a method for the diagnosis and/or prognosis and/or therapeutic monitoring of Huntington's disease in humans.

In one embodiment, a sample is obtained from a subject.

In one example, the sample comprises a cell sample. In another example, the sample comprises a tissue sample. In another example, the sample comprises a bodily fluid. Methods of sample collection are well known to the skilled worker.

The term "tissue sample" or "tissue", as used herein, refers to an aggregate of cells usually of a particular kind together with their intercellular substance that form one of the structural materials of a plant or an animal and that in animals include connective tissue, epithelium, mucosal membrane, muscle tissue, and nerve tissue, and the like.

The term "bodily fluid", as used herein, refers to a naturally occurring fluid from a human or an animal, and includes, but is not limited to cerebral spinal fluid, feces, semen, products of lactation or menstruation, cervical secretions, vaginal fluid, urine, mucous, gastric juices, pancreatic juices, bone marrow aspirates, tears, lymph saliva, sputum, serum, plasma, blood, pharyngeal, nasal/nasal pharyngeal and/or sinus secretions.

The term "cell", as used herein, refers to any cell type.

In a specific example, the cell sample comprises a fibroblast.

In a specific example the bodily fluid is a blood sample.

In a specific example, the sample comprises white blood cells, lymphocytes, fibroblasts, amniotic fluid, chorionic tissue or cerebral spinal fluid.

A marker is used to assay and/or assess the sample collected from the subject(s).

A variety of machines and/or instrumentation are used to detect and/or measure the marker within the sample.

In one example, cholera toxin B is used to detect GM1 within the sample. In this example, binding of cholera toxin B to GM1 results in formation of a complex which is detected/measured. Such detection/measurement methods include, but are not limited to, ELISA, dot-blots, flow cytometry, in-cell westerns or fluorescent microscopy.

In another example, GM1 is detected in a sample using mass spectroscopy.

In another example, an antibody directed to GM1 is used to detect GM1 within the sample. In this example, binding of the antibody to GM1 results in the formation of a complex which is detected/measured. In a specific example, rabbit polyclonal anti-GM1 (Calbiochem) is used. In another example, N17pS13pS16 antibody is used. Such antibodies are used to detect GM1 using methods including, but not limited to, ELISA, dot-blots, flow cytometry, in-cell westerns or fluorescent microscopy.

In another aspect of the present invention, there is provided a method of gene expression analysis of GM1/GD1b/GT1c synthase gene (also known as B3GalT4 or Gal-T2, UDP-Gal: betaGleNAcbeta 1,3-galactosyltransferase polypeptide 4), which encodes the enzyme that produces GM1. Expression levels of this gene are decreased in HD cells. Therefore, the levels of the gene can be used as a diagnostic to predict onset and/or development of Huntington's disease. Methods including, but not limited to, real-time PCR and quantitative PCR using primers specific for the gene, and northern blotting using specific probes for the gene can be used.

In the example of gene expression analysis, the skilled worker will appreciate that a variety of sample source can be used from which to detect the B3GalT4 gene expression.

In a specific example, the detection and/or measurement of GM1 within the sample is carried out using confocal microscopy of Alexa594-cholera toxin B binding to the GM1 within the sample. In one example, the confocal microscope is a LSM510 laser scanning confocal microscope mounted on a Zeiss Axiovert 100M microscope.

In another specific example, the detection and/or measurement of GM1 within the sample is carried out using flow cytometry (FACS) of Alexa488-conjugated cholera toxin B binding to GM1 within a cell. In one example, FACS analysis is performed using a FACSCalibur flow cytometer.

In another specific example, the detection and/or measurement of GM1 within the sample is carried out using dot-blot analysis of HRP-conjugated cholera toxin B subunit. In one example, dot blot analysis is performed using nitrocellulose membrane. In a specific example the nitrocellulose membrane is Trans-Blot® Transfer Medium nitrocellulose membrane.

In another example, GM1, GD1a, and GT1b are detected by thin layer chromatography.

In another specific example, the detection and/or measurement of GM1, GD1a, and GT1b within the sample is carried out using thin-layer chromatography (TLC) analysis of the sample compared to known standards.

In one example, there is provided a method comprising: a) obtaining a sample from a subject, b) contacting the sample with cholera toxin B to form a complex between the cholera toxin B and GM1 in the sample; c) measuring and/or detecting the complex formed to determine an amount of GM1 in the sample; d) determining the onset and/or development of Huntington's disease, wherein the onset and/or development of Huntington's disease is indicated by the level of GM1 in the sample.

In another example, there is provided a method comprising: a) obtaining a sample from a subject, b) analyzing the sample, and optionally a control, using a confocal microscope, a flow cytometer, or dot-blotting, having a detector set to detect a complex formed between cholera toxin B and GM1 within the sample; and c) determining the onset and development of Huntington's disease, wherein the development of Huntington's disease is indicated by the level of GM1 in the sample.

In accordance with another aspect of the present invention, there is provided a method comprising: a) obtaining a sample from a subject, b) analyzing the sample using thin layer chromatography in accordance with known methods in the art (Ladisch and Gillard, 1985; Wu et al. 2001; Ledeen and Yu, 1982; Svennerholm 1957); and c) determining the onset and/or development of Huntington's disease, wherein the onset and/or development of Huntington's disease is indicated by the level of GM1 in the sample.

In another aspect of present invention, the methods of the present invention permit the determination of the age of HD onset as indicated by the level of GM1 and/or GD1a and/or GT1b, and/or B3GalT4 gene expression, or combinations thereof in the sample from a subject.

In another example, there is provided a method comprising: a) obtaining a sample from a subject; and b) analyzing the sample to identify GM1, wherein the determining the onset and/or development of Huntington's disease in the subject is indicated by the level of GM1 in the sample.

In another example, there is provided a method comprising: a) obtaining a sample from a subject; and b) analyzing the sample to identify B3GalT4 gene expression, wherein the determining the onset and/or development of Huntington's disease in the subject is indicated by the level of B3GalT4 mRNA in the sample.

In another example, there is provided a method comprising: a) obtaining a sample from a subject; and b) analyzing the sample to identify GD1a, wherein the determining the onset and/or development of Huntington's disease in the subject is indicated by the level of GD1a in the sample.

In another example, there is provided a method comprising: a) obtaining a sample from a subject; and b) analyzing the sample to identify GT1b, wherein the determining the onset and/or development of Huntington's disease in the subject is indicated by the level of GT1b in the sample.

In one example, there is provided a method comprising: administering to a subject for treatment and/or prevention of Huntington's disease, an effective therapeutic amount of GM1.

In one example, GM1 is commercially available. In another example, GM1 is synthetically produced.

In one example, there is provided a method comprising: administering to a subject for treatment and/or prevention of Huntington's disease, an effective therapeutic amount of GM3.

In one example, GM3 is commercially available. In another example, GM3 is synthetically produced.

In another example, there is provided a method comprising, administering to a subject for the treatment of Huntington's disease an effective therapeutic amount of GM1, wherein the GM1 administered results in (i) increased levels of GM1 in the HD cells in the subject or (ii) reduces the susceptibility of the HD cells in the subject to apoptosis as compared to untreated HD cells, (iii) increased phosphorylation of mHtt, or (vi) combinations thereof.

In another example, there is provided a use of GM1 and/or GM3 in the manufacture of a medicament suitable for the treatment of Huntington's disease.

In another example, there is provided a use of GM1 and/or GM3 suitable for the treatment of Huntington's disease.

In another example, there is provided a use of GM1 for increasing the amount of phosphor-mHtt in a cell.

In another example, there is provided a use of GM1 and/or GM3 for protecting HD cells from apoptosis.

Methods of GM1 and/or GM3 administration include, but are not limited to, intraventricular infusion, liposomal delivery and ultrasound-mediated delivery (UTMD). As the skilled worker will appreciate, UTMD relies on the introduction of macromolecules that have been immobilized on gas mircobubbles into the general circulation, followed by their site-directed destruction by focused ultrasound. Ultrasound pulses transiently open up pores in cell membranes and also disrupt the blood brain barrier, allowing the uptake of drugs into the brain. The method of IT, ICV and intraparenchymal administration are described above.

The method(s) of the present invention can be automated, the data being sent to a computer that analyzes the amount of cholera B toxin—GM1 complex, anti-GM1 antibody-GM1 complex in a sample, anti-GD1a-GD1a complex in a sample, anti-GT1b-GT1b complex in a sample and/or the amount of B3GalT4 mRNA in a sample.

Methods of the present invention are conveniently practiced by providing the compound(s) and/or composition(s) used in such method in the form of a kit. Such a kit preferably contains instructions for the use thereof.

To gain a better understanding of the invention described herein, the following examples are set forth. It should be understood that these examples are for illustrative purposes only. Therefore, they should not limit the scope of this invention in any way.

EXAMPLES

Example I

Experimental Procedures

Animal and Cell Models

YAC128 mice were purchased from the Jackson Laboratories (Jackson Laboratories, Bar Harbor, Me., USA). Female YAC128 mice were crossed with male FVB/N wild-type mice for colony maintenance. All procedures on animals were approved by the University of Alberta's Animal Care and Use Committee and were in accordance with the guidelines of the Canadian Council on Animal Care.

Conditionally-immortalized rat striatal ST14A cells and ST14A cells expressing an N-terminal fragment of mHtt containing 120 glutamines (N548-120Q) were kindly provided by Dr. E. Cattaneo (University of Milan, Italy) and maintained in culture at the permissive temperature (33° C.) as previously reported (Rigamonti et al., 2001). Conditionally-immortalized mouse striatal knock-in cells expressing endogenous levels of wild-type (STHdh$^{Q7/Q7}$) or mHtt (STHdh$^{Q111/Q111}$) were a gift from Dr. M. E. MacDonald (Massachusetts General Hospital, Boston, Mass., USA) and were maintained as previously described (Trettel et al., 2000). Human skin fibroblasts isolated from HD patients were purchased from the Coriell Cell Repositories (Coriell Institute for Medical Research, Camden, N.J., USA) and grown in modified Eagle's Medium (MEM, Invitrogen) supplemented with 15% fetal bovine serum (FBS), 2 mM L-glutamine, 100 U/mL penicillin, 100 µg/mL streptomicin and 0.11 g/L sodium pyruvate (all from Invitrogen).

Primary Cultures of Neurons and Astrocytes

Cultures of primary cortical and striatal neurons were prepared from newborn mice (P0)

Briefly, the brain was dissected and selected regions were minced and digested with 1 mg/ml papain for 10 min at 37° C. DNAse was added to the digestion mix in the last 5 min of incubation. Cells were centrifuged at 200×g for 1 min, resuspended in Neurobasal-A medium (Invitrogen) supplemented with 1% B27 (Invitrogen) and gently dissociated by pipetting up and down. Neurons were plated onto poly-D-lysine-coated wells at a density of $0.1 \times 10^6$ cells/cm$^2$ and used for experiments at 9-11 days in vitro. Astrocytes were isolated from two day-old (P2) mice and maintained in culture for 20 days as previously described (Karten et al., 2005).

Confocal Microscopy of Cholera Toxin B Surface Binding

Cells were seeded onto glass coverslips coated with 50 µg/ml poly-L-lysine. The day after, cells were fixed in 4% paraformaldehyde at room temperature for 10 minutes, and then incubated in 1.5 mg/ml glycine in PBS for 10 minutes at room temperature, followed by 10 µg/ml Alexa594-conjugated cholera toxin B (Molecular Probes, Invitrogen) in PBS/0.1% BSA for 20 minutes at 4° C. Slides were analyzed with an LSM510 laser scanning confocal microscope mounted on a Zeiss Axiovert 100M microscope. Images of wild-type and HD cells were acquired using the same confocal settings. Z-stack images were compressed into a single projection image.

Determination of CAG Number in the HD Gene of Human Fibroblasts

Twenty ng of genomic DNA were amplified by PCR using primers for the human HD gene sequence flanking the CAG repeats (forward primer: CCGCTCAGGTTCTGCTTTTA; reverse primer: GGCTGAGGAAGCTGAGGAG) The amplification product was sequenced at the University of Alberta DNA Core Facility.

Determination of Plasma Membrane and Total GM1 Content by Flow Cytometry (FACS)

Plasma membrane and total GM1 levels were measured by cholera toxin B subunit binding (Holmgren et al., 1975) and FACS analysis. For plasma membrane binding, cells were trypsinized, washed in ice-cold Hank's Balanced Salt Solution (HBSS, Invitrogen) and labeled with 2 µg/ml Alexa488-conjugated cholera toxin B (Molecular Probes, Invitrogen) in PBS/0.1% fat-free BSA for 5 minutes at 4° C. Under these conditions intracellular transport and internalization of cholera toxin are inhibited and therefore only the GM1 present at the plasma membrane is labeled. After washing, cells were fixed with 2% paraformaldehyde and stored at +4° C. until FACS analysis was performed. For analysis of total GM1 content, cells were fixed in 2% paraformaldehyde for 30 minutes and incubated for 1 hour at room temperature in 4 µg/ml Alexa 488-conjugated cholera toxin B in PBS containing 0.3% saponin and 1% BSA. FACS analysis was performed using a FACSCalibur flow cytometer and CellQuest software (BD Biosciences).

Determination of Total GM1 Content by Dot-Blotting

Cells were lysed in Tris-buffered saline (TBS) containing 0.1% Tween-20 (TBS-T) and protease inhibitors cocktail (1:100, SIGMA-Aldrich, St. Louis, Mo., USA), and homogenized by repeated passages through a 1-ml syringe with a 26-gauge needle. Two µl of cell lysate (about 100 ng of proteins) were spotted onto Trans-Blot® Transfer Medium nitrocellulose membrane (Bio-Rad Laboratories, Hercules, Calif., USA). Non-specific binding to the membrane was blocked with 5% milk in TBS-T for 1 hour at room temperature. The membrane was then incubated for 30 minutes at room temperature in 400 ng/ml HRP-conjugated cholera toxin B subunit (Invitrogen, Eugene, Oreg., U.S.A.) in 5% milk/TBS-T. Visualization was performed by ECL Plus (Amersham Biosciences).

Analysis of Gangliosides by Thin-Layer Chromatography (TLC)

Tissue (striatum and cortex) or cultured cells were homogenized in 10 mM Tris-HCl, pH 7.4 containing 1 mM DTT. Total lipids (TL) were extracted from tissue (1 mg of protein) or cells (10 mg of protein) in $CHCl_3:CH_3OH:H_2O$ (4:8:3), and particulate material was removed by centrifugation at 750×g at 4° C. for 10 minutes.

Gangliosides were isolated from TL extracts as previously described (Ladisch and Gillard, 1985). Briefly, the TL extract was dried under a stream of nitrogen and the residue was dissolved in di-isopropyl ether:buthanol:50 mM NaCl (3:2:2.5 v/v/v). Gangliosides partitioning into the lower aqueous phase were recovered and dried under nitrogen. The residue was dissolved in sterile water and desalted by gel filtration using a Sephadex G-50 (SIGMA-Aldrich, St. Louis, Mo., USA) column. The eluate was collected in 0.5 ml fractions and the presence of gangliosides in the fraction was confirmed by reading the adsorbance of each fraction at 206 nm. Fractions containing gangliosides (fractions 5 to 10) were pooled, lyophilized and re-dissolved in $CH_3OH:CHCl_3$ (1:1 v/v). Gangliosides were then spotted onto TLC plates (EMD Chemicals Inc., Gibbstown, N.J., USA) and separated with $CHCl_3:CH_3OH:0.25\%$ KCl (5:4:1 v/v/v) (Wu et al., 2001). Ganglioside bands were revealed by reaction with resorcinol (0.2% resorcinol, 80% HCl, 0.25 mM $CuSO_4$) in oven at 120° C. for 15 minutes (Ledeen and Yu, 1982; Svennerholm, 1957) and identified by comparison with a standard ganglioside mix (Matreya, Pleasant Gap, Pa., USA). Relative quantitation of ganglioside bands was performed by densitometric analysis using Quantity One® software (Bio-Rad Laboratories, Hercules, Calif., USA).

RNA Extraction and Real-Time PCR Analysis of Gene Expression

Total RNA was extracted using RNeasy kit (Qiagen) according to the manufacturer's instructions. For analysis of gene expression in cell lines and human fibroblasts, total RNA was prepared from cells at three consecutive passages in culture. All samples were subjected to in-column treatment with DNaseI (Qiagen) to eliminate genomic DNA contamination. One µg of total RNA was reverse-transcribed using Superscript II reverse transcriptase (Invitrogen) and oligo-d (T) primer, and resulting cDNAs were amplified using Power SYBR® Green PCR Master Mix (Applied Biosystems), following manufacturers' instructions. Gene-specific primers were designed using Primer Express 3.0 software (Applied Biosystems, Foster City, Calif., USA). Primer sequences are listed in FIG. 12. Quantitative PCR analysis was carried out on a StepOnePlus™ instrument (Applied Biosystems, Foster City, Calif.), by comparison with a standard curve generated by cDNA serial dilutions. The level of each mRNA was normalized to that of cyclophilin A. PCR cycling parameters were: 50° C. for 2 minutes, 95° C. for 5 minutes, followed by 40 cycles of 95° C. for 20 seconds, 60° C. for 1 minute and 72° C. for 40 seconds.

Induction and Measurement of Apoptosis

In order to induce apoptosis immortalized cells were incubated at 39° C. (Cattaneo and Conti, 1998; Trettel et al., 2000) in serum-free medium for the indicated time. For apoptosis detection, at the end of each treatment cells were collected, washed with PBS and incubated with PE-conjugated annexin V (BD Biosciences) according to the manufacturer's instructions. For the simultaneous detection of active caspase-3 and annexin V binding, cells were first labeled with annexin V as indicated above, then fixed in 4% paraformaldehyde and permeabilized with 0.3% saponin in PBS containing 4% donkey serum. Cells were then incubated for 1 h with FITC-conjugated anti-active caspase-3 antibody (1:200 BD Biosciences) and analyzed with a FACSCalibur flow cytometer and CellQuest software (BD Biosciences).

Treatments with Ganglioside GM1 and Inhibitors

GM1 (Alexis) at the indicated concentrations was added to the cells in serum-free medium at the time when cells were shifted at 39° C. to induce apoptosis.

To inhibit ganglioside synthesis, wild-type cells were incubated for 3 days in medium containing 10 µM 1-phenyl-2-palmitoylamino-3-morpholino-1-propanol (PPMP, Matreya, Pleasant Gap, Pa., USA). Cells were then washed two times with PBS and incubated for 12 hours at 39° C. in serum-free medium to induce apoptosis.

K252a (200 nM, Calbiochem) was used to inhibit TrK receptor-mediated signaling. Triciribin (TCN, 1 µM—BIOMOL International) was used to inhibit AKT activation. Both inhibitors were administered to the cells 2 hours before induction of apoptosis and administration of GM1.

Huntingtin Immunoprecipitation

Cells were pre-incubated for 5 hours at 33° C. in serum-free medium, treated with 50 µM GM1 (Alexis) for 5 minutes, and then lysed with RIPA buffer (20 mM Tris, pH 8.0, 150 mM NaCl, 1% Triton X-100, 0.5% Na-deoxycholate, 0.1% SDS, 1 mM EDTA) containing protease inhibitor cocktail (1:100, Sigma) and phosphatase inhibitors (1 mM NaF, 1 mM Na$_3$VO$_4$). For immunoprecipitation, protein G-Sepharose (Zymed, Invitrogen) was complexed with monoclonal anti-Htt antibody (mab2166, Chemicon) overnight at 4° C. and then incubated with 1 mg of total protein extracts for 4 hours at room temperature. The immunoprecipitated protein was resolved on 6% SDS-PAGE and detected by immunoblotting with anti-Htt (1:5000, Chemicon) and anti-phosphoSer (1:200, Abcam).

Immunoblotting

Cells were scraped in 10 mM Tris-HCl, pH 7.4, containing 1% NP40, 10 mM NaF, 1 mM Na$_2$VO$_4$ and 1:100 protease inhibitor cocktail (SIGMA-Aldrich, St. Louis, Mo., USA) and lysed by sonication followed by incubation on ice for 30 minutes. Cell debris were removed by centrifugation at 15,000×g for 15 minutes. Protein concentration in the supernatant was measured by BCA assay (Pierce). Thirty μg of proteins were resolved on 10% SDS-PAGE and transferred to nitrocellulose membranes (Bio-Rad Laboratories, Hercules, Calif., USA). Membranes were blocked with 5% non-fat milk in TBS-T (50 mM Tris-HCl, 150 mM NaCl, pH 7.4, 0.1% Tween 20) for 1 hour and then probed overnight with primary antibodies: anti-phospho-AKT (Ser473) (1:500), anti-AKT (1:500) (both from Cell Signaling), Abcam). HRP-conjugated secondary antibodies were used at 1:3,000 dilution (Bio-Rad Laboratories, Hercules, Calif., USA). Protein bands were detected by ECL Plus (Amersham Biosciences) and analyzed with Quantity One® software (Bio-Rad Laboratories, Hercules, Calif., USA).

Statistical Analysis

Statistical significance was calculated by two-tailed t-test and by the ANOVA/Dunnet test (for the data generated in fibroblasts from patients), using Prism 4.0 software (Graphpad software, Inc.).

Results

Striatal HD Cells and Human Skin Fibroblasts Isolated from HD Patients have Decreased GM1 Content Two striatal cell models of HD were employed: knock-in striatal cells, in which the expression of physiological levels of either wild-type (STHdh$^{Q7/Q7}$) or mutant Htt (STHdh$^{Q111/Q111}$) is controlled by the endogenous mouse Hd promoter (Trettel et al., 2000); and immortalized rat striatal cells expressing endogenous wild-type Htt (ST14A) or over-expressing an N-terminal fragment of mHtt containing 120 glutamines (N548-120Q).

Expression of mHtt (either full-length or truncated) resulted in lower plasma membrane binding of cholera toxin B, a protein that specifically recognizes the ganglioside GM1 (Holmgren et al., 1975), indicating that a lower amount of GM1 is present at the plasma membrane of HD cells than in wild-type controls (FIGS. 1A and 1B). Knock-in STHdh$^{Q111/Q111}$ cells contained 25% less GM1 at the plasma membrane than STHdh$^{Q7/Q7}$ cells (FIG. 1B). Levels of this ganlioside were further decreased in cells expressing the N-terminal fragment of mHtt (FIGS. 1A and 1B).

GM1 is synthesized in the Golgi apparatus and then transported to the plasma membrane (Tettamanti, 2004). To exclude the possibility that lower levels of GM1 in the plasma membrane of HD cells resulted from impaired Golgi-to-plasma membrane traffic, the total amount of GM1 present in HD cells was measured. Had ganglioside transport been impaired, similar levels of total GM1 in wild-type and HD cells (or even an increase of total GM1 in HD cells due to intracellular ganglioside accumulation) would have been expected to be observed. Instead, total levels of GM1 mirrored the plasma membrane GM1 content, suggesting that synthesis of the ganglioside, rather than its transport, might be affected in HD cells (FIG. 1C). To confirm these data, cell GM1 content was analyzed by lipid extraction and ganglioside separation by TLC. Results were virtually identical to those generated with the use of cholera toxin B (FIG. 1D).

Plasma membrane levels of GM1 in primary fibroblasts derived from 4 different HD patients and 2 age-matched control subjects (FIG. 11) was assessed. Since ganglioside synthesis may be influenced by cell density and number of passages in vitro (Sciannamblo et al., 2002), all studies were performed on cells at the same passage number and cell confluence. As shown in FIG. 1E, human HD fibroblasts had lower levels of ganglioside GM1 compared to age-matched control lines.

Figure 2:
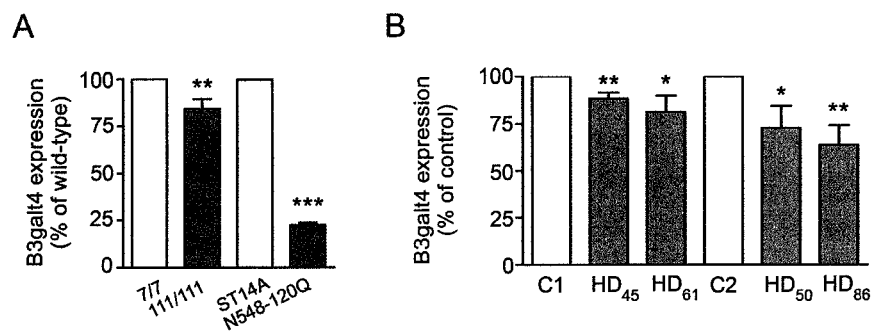

The expression of B3galt4, the gene encoding GM1/GD1b/GT1c synthase, was significantly down-regulated in mutant knock-in cells (FIG. 2A) and human HD fibroblasts (FIG. 2B), compared to controls. These data suggest that decreased ganglioside levels in HD cells are due to reduced biosynthesis.

Mutant Huntingtin Affects Ganglioside Metabolism in the Brain of HD Mice

Figure 3:
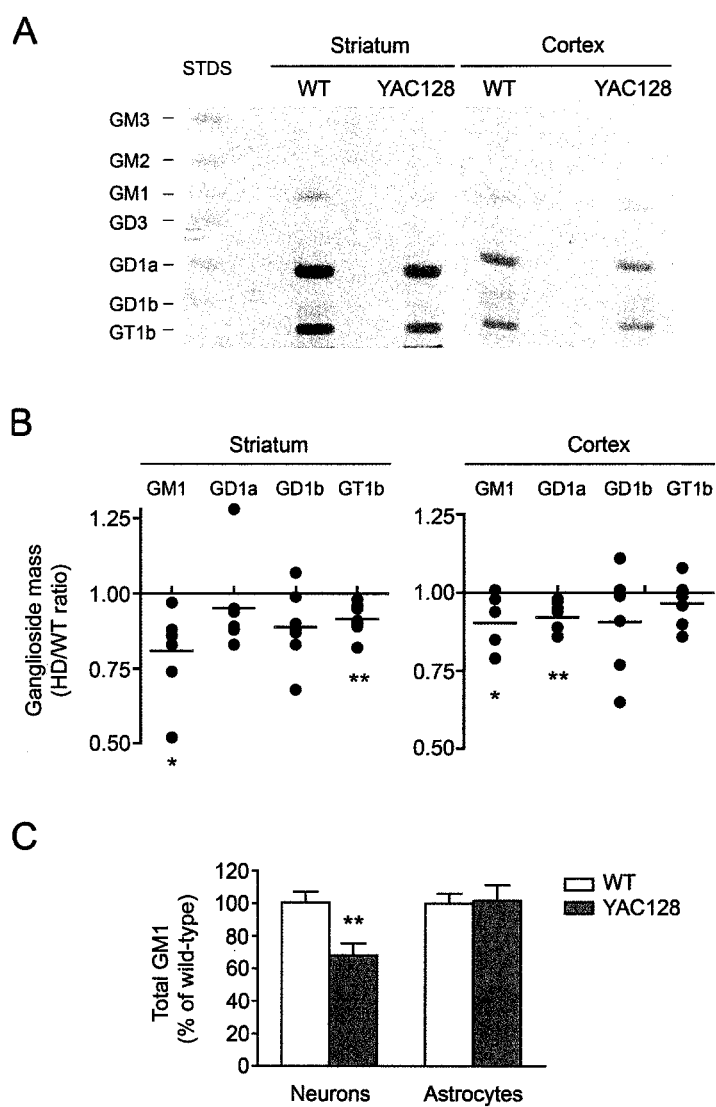

In order to establish whether mHtt affects ganglioside metabolism in the brain in vivo, a well-characterized model of HD, the YAC128 mouse, which recapitulates many aspect of the human pathology (Slow et al., 2003) was studied. In agreement with the data obtained in cell lines, analysis of gangliosides in 6 month-old YAC128 mice (by lipid extraction and TLC separation) showed that GM1 levels were reduced in both striatum and cortex, the areas of the brain that are most affected in HD (FIGS. 3A and 3B). In addition, two other major gangliosides in the brain, GD1a and GT1b, were significantly decreased in YAC128 cortex and striatum, respectively. Dot-blotting for GM1 revealed that in YAC128 primary neurons the GM1 deficit was much more pronounced (about 32% compared to wild-type) than observed in tissue in toto, while no deficit was detectable in YAC128 astrocytes (FIG. 3C). While not wishing to be bound by theory, since astrocytes also express mHtt (Singhrao et al., 1998), these data suggest that mHtt affects ganglioside metabolism in a cell-specific manner, and that the small GM1 deficit observed in brain tissue analyzed in toto, actually reflects much larger changes at the cellular level.

The synthesis of each specific ganglioside and the overall ganglioside expression profile depends on the activity of multiple enzymes, the cell-specific formation of enzyme complexes and the flux of intermediates through the pathway (Yu et al., 2004). A simplified scheme of the biosynthetic pathway for the major gangliosides is illustrated in FIG. 4A.

Figure 4:
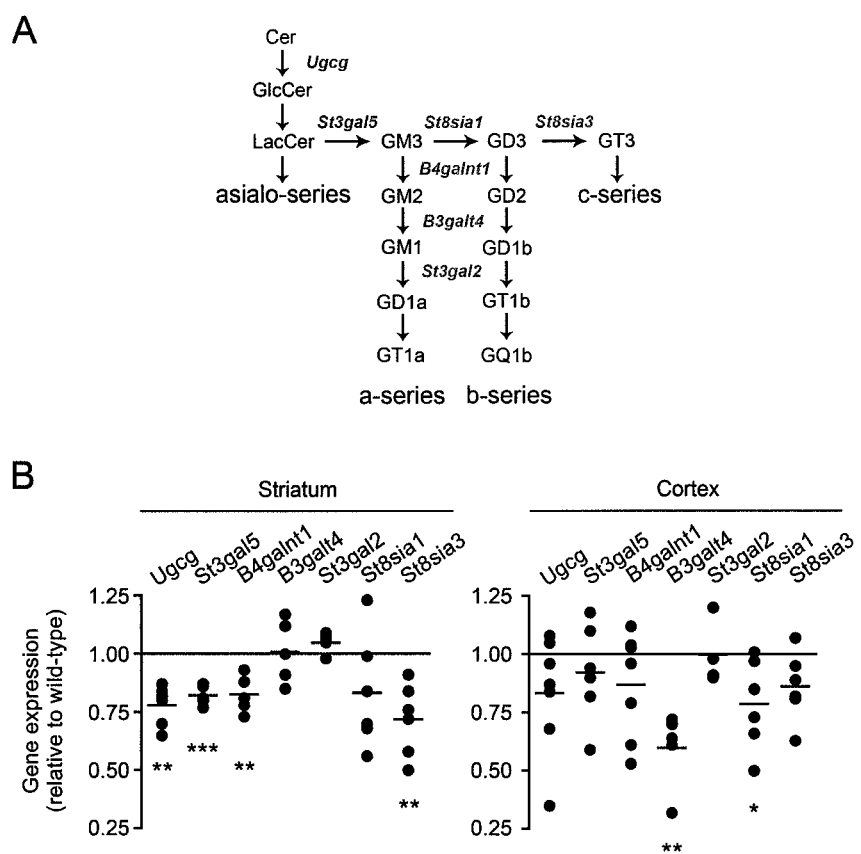
FIG. 4—Specific enzymes of the ganglioside biosynthetic pathway are down-regulated in striatum and cortex of YAC128 mice. A) Simplified scheme of the ganglioside biosynthetic pathway. Critical enzymes in the pathway are indicated in red. Gangliosides of the asialo-series and of the c-series are less abundant and were omitted to improve clarity. B) Analysis of gene expression in YAC128 mice by real-time PCR. Each dot represents an individual animal. From five to six animals were used in the analysis. Lines indicate the mean value in each group. Data are expressed as ratios of HD over wild-type. *, $p<0.05$; , $p<0.001$; *, $p<0.0001$ FIG. 5—GM1 administration raises plasma membrane ganglioside levels and protects cells from apoptosis. Cells were incubated with or without 50 μM GM1 and exposed to apoptotic conditions (serum deprivation at 39° C.). A) Representative FACS profile of cells after 12 hours incubation in apoptotic conditions. Cells were labeled with Annexin V and then stained for active caspase-3. FL1-H and FL2-H indicate fluorescence intensity for active caspase-3 and annexin V stainings, respectively. Double positive cells in the upper right quadrant are apoptotic cells. Annexin V-positive, but active caspase 3-negative cells (upper left quadrant) are early apoptotic cells. The number reported in each quadrant represents the percentage of cells in the quadrant. B) Quantitation of apoptotic cells by FACS analysis of annexin V-binding. Data are the mean±SD of 4 experiments, each performed in triplicate. C) Plasma membrane GM1 levels were measured after GM1 administration by analysis of cholera toxin B binding. Data are expressed as percentage of control (wild-type in basal conditions) and represent the mean±SD of 3 experiments, each performed in triplicate. 7/7, STHdh$^{7Q/7Q}$; 111/111, STHdh$^{111Q/111Q}$; *, $p<0.05$; , $p<0.001$; *, $p<0.0001$ FIG. 6—Inhibition of GM1 biosynthesis renders wild-type cells more susceptible to apoptosis. Cells were treated with 10 μM PPMP, an inhibitor of the ganglioside biosynthetic pathway, for 3 days and then exposed to apoptotic conditions (serum deprivation at 39° C.). A) Plasma membrane levels of GM1 were measured by cholera toxin B-binding and FACS analysis after incubation with PPMP. B) The percentage of apoptotic cells upon incubation of the cells for 12 hours in serum-free medium was measured by annexin V binding. Data are the mean±SD of 3 experiments. 7/7, STHdh$^{7Q/7Q}$; 111/111, STHdh$^{111Q/111Q}$; *, $p<0.05$; , $p<0.001$; *, $p<0.0001$ FIG. 7—GM1 protective effect on striatal cells is partially mediated by AKT activation. A) Akt phosphorylation was measured 7 minutes and 6 hours after addition of GM1 in serum-free medium and incubation at 39° C. to induce cell death. Analysis of phospho-AKT/AKT ratio, indicative of AKT activation, was performed by densitometric analysis of immunoblots in three independent experiments. In each experiment, the pospho-AKT/AKT ratio measured in wild-type untreated cells (control) was arbitrarily set to 100% to which HD and GM1-treated samples were compared. Mean values±SD and representative immunoblots are shown. B) Cells were pre-incubated for 2 hours with 1 μM triciribin (TCN), an inhibitor of AKT activation, before GM1 administration and exposure to apoptotic stress (serum-free medium at 39° C.). The percentage of apoptotic cells was measured by annexin V binding. Data are the mean±SD of 3 experiments, each performed in triplicate. 7/7, STHdh$^{7Q/7Q}$; 111/111, STHdh$^{111Q/111Q}$; *, $p<0.05$; , $p<0.001$; *, $p<0.0001$ FIG. 8—Administration of GM1 increases levels of phospho-mHtt. STHdh$^{111Q/111Q}$ cells were incubated with or without GM1 for 5 minutes. Mutant Htt was immunoprecipitated and its phosphorylation state was assessed by immunoblotting with anti-phospho-Ser antibody. A representative immunoblot is shown, along with the densitometric analysis performed on three independent experiments. In each experiment, the ratio phospho-Ser/mHtt measured in untreated cells was arbitrarily set to 1, and the ratio obtained for GM1-treated cells was compared to it. FL-mHtt, full-length mHtt; *, $p<0.05$.
Figure 15:
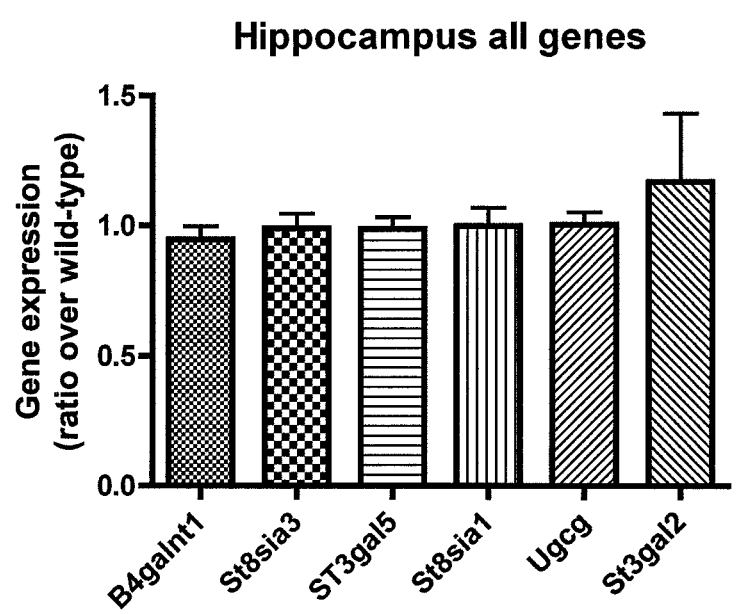
FIG. 15—Expression of genes in the ganglioside biosynthetic pathway in the hippocampus of YAC128 (HD) mice compared to wild-type littermates. Gene expression analysis was performed by real-time PCR on tissue isolated from 4-5 mice. Data are expressed as ratios of HD over wild-type.

In line with the biochemical data, the expression of genes encoding enzymes in the pathway, specifically Ugcg, St3gal5 (also known as GM3 synthase), B4galnt1 (GM2/GD2 synthase), St8sia1 (GD3 synthase) and St8sia3 (GT3 synthase), were significantly down-regulated in YAC128 mice compared to wild-type littermates (FIG. 4B). Expression of GM1 synthase (B3galt4) was significantly decreased in the YAC128 cortex, but not in the striatum. However, down-regulation of upstream enzymes in the pathway may well explain the overall reduced GM1 mass in the striatum of YAC128 mice. No gene expression changes were detected in the hippocampus, a brain area that is less affected in HD (FIG. 15)

Figure 9:
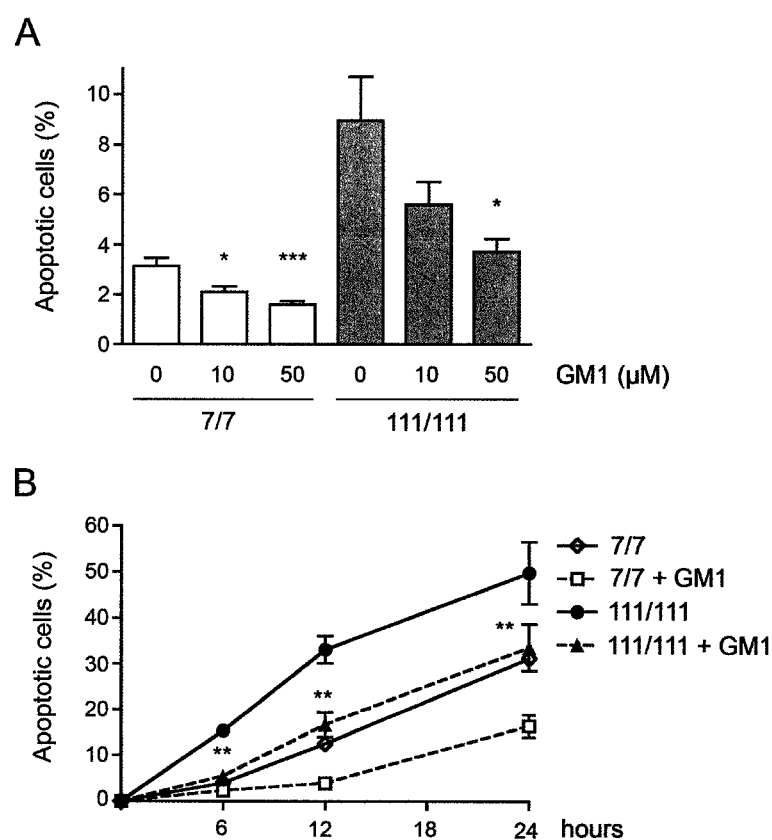
FIG. 9—Dose-dependency and time-course of GM1 anti-apoptotic action in knock-in striatal cells. A) Cells were incubated in serum-free medium at 39° C. to induce apoptosis, in the presence of the indicated concentration of GM1. After 6 hours, apoptosis was measured by Annexin-V binding and FACS analysis. B) Cells were incubated as indicated in A) in the presence or absence of 50 μM GM1. Apoptosis was assessed by Annexin-V binding and FACS analysis at the indicated time, over a period of 24 h. Data are reported as mean values±SD. 7/7, STHdh$^{7Q/7Q}$; 111/111, STHdh$^{111Q/111Q}$; *, $p<0.05$; **, $p<0.001$ FIG. 10—The protective effect of GM1 in striatal cells is not mediated by activation of Trk receptors. Cells were pre-incubated for 2 hours with 200 nM K252a, a pan-Trk inhibitor, before GM1 administration and exposure to apoptotic stress (serum-free medium at 39° C.). Data are the mean±SD of 3 experiments, each performed in triplicate. 7/7, STHdh$^{7Q/7Q}$; 111/111, STHdh$^{111Q/111}$Q; *, $p<0.05$; , $p<0.001$; *, $p<0.0001$ FIG. 11—Human fibroblasts and HD patients' statistics. Age at biopsy indicates the age of the patients when skin fibroblasts were donated.

Administration of GM1 to HD Cells Restores Ganglioside Levels and Protects Cells from Apoptosis The effect of GM1 on HD cells was examined. Striatal knock-in cell lines were used, since these cells are a precise genetic model of HD without the caveats potentially associated to transgene over-expression. Apoptotic cell death was assessed by measuring caspase-3 activation, as well as phosphatidylserine externalization (an early marker of apoptosis) by annexin V-binding. Similar results were obtained with the two assays (FIG. 5A). HD cells (knock-in STHdh$^{111Q/111Q}$) were more prone to undergo apoptosis than wild-type cells (STHdh$^{7Q/7Q}$) when grown in the absence of serum, and showed increased levels of active caspase-3 (FIG. 5A) and increased annexin V binding (FIG. 5B). Administration of GM1 protected both wild-type and HD cells from apoptosis (FIG. 5B) in a dose-dependent manner (FIG. 9). GM1 restored normal susceptibility to apoptosis in HD cells, which, upon treatment with the ganglioside, became indistinguishable from control wild-type cells (FIG. 5B). Protection from apoptosis in HD cells occurred in parallel to complete restoration of GM1 levels upon ganglioside administration (FIG. 5C). In treated wild-type cells, where the incorporation of exogenous GM1 resulted in a further increase of GM1 content above their normal levels, cell survival was also further augmented. While not wishing to be bound by theory, these results suggest that GM1 modulates cell response to stress and that HD cells are more susceptible to apoptosis because of lower GM1 content.

Figure 6:
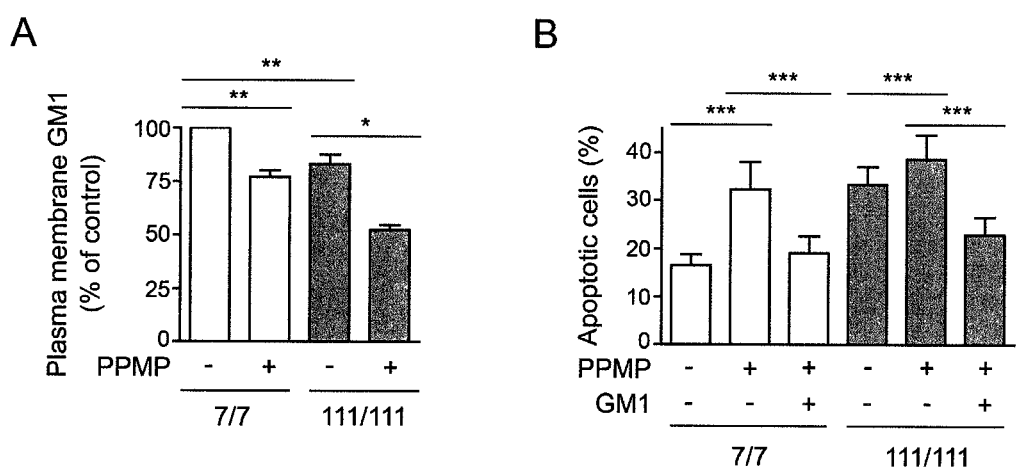

Inhibition of Ganglioside Biosynthesis in Wild-Type Cells Increases Cell Susceptibility to Apoptosis and Recapitulates STHdh111Q/111Q Cells Phenotype To examine the effect of GM1 levels on susceptibility to apoptosis in HD cell, GM1 synthesis was inhibited in wild-type STHdh$^{7Q/7Q}$ cells to reduce GM1 levels to the amount observed in STHdh$^{111Q/111Q}$ cells (FIG. 6A). This was achieved by incubating wild-type cells for 3 days with 10 µM 1-phenyl-2-palmitoylamino-3-morpholino-1-propanol (PPMP), a well-known inhibitor of glucosylceramide synthase (Ugcg, FIG. 4A) (Abe et al., 1992), the enzyme that catalyzes the first reaction committed to ganglioside biosynthesis. PPMP treatment increased STHdh$^{7Q/7Q}$ cell susceptibility to apoptosis to the levels observed in STHdh$^{111Q/111Q}$ cells (FIG. 6B). Administration of GM1 abolished PPMP effects, thus demonstrating that the increased susceptibility to apoptosis was specific to decreased levels of GM1, rather than to the accumulation of metabolic precursors of the ganglioside. These data confirm that even a small reduction in GM1 synthesis is sufficient to sensitize cells to stress. They also demonstrate that GM1 deficit in HD cells is the trigger of their heightened response to apoptotic stimuli.

Figure 7:
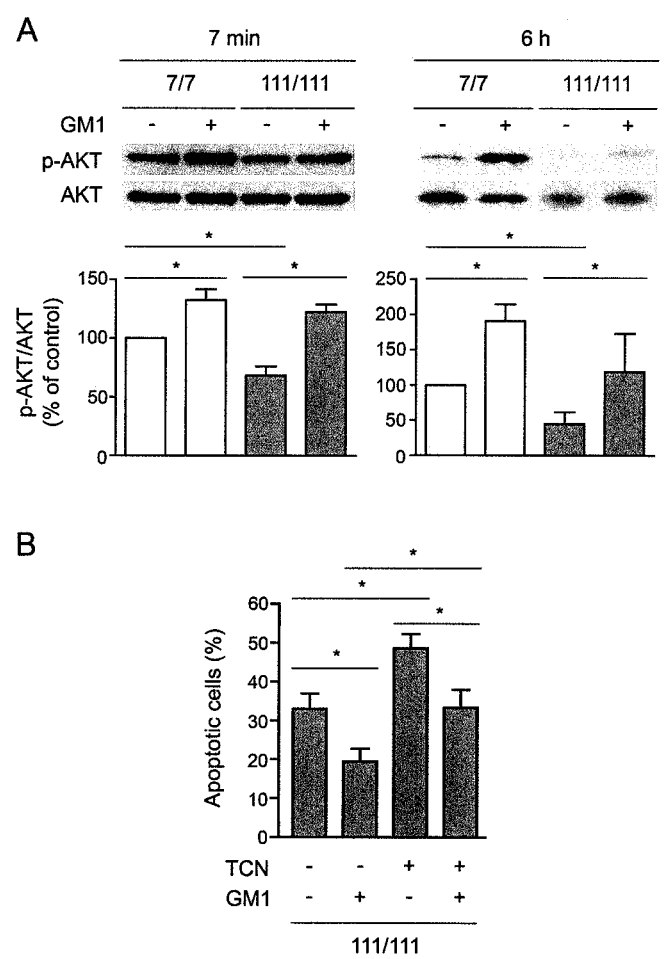

GM1 Promotes the Activation of AKT in HD Cells, Independently of Trk Receptor Stimulation It was next examined whether the pro-survival action of GM1 was mediated by AKT activation, since the PI3K/AKT pathway is the most important pathway contributing to neural survival. In basal conditions (absence of GM1), STHdh$^{111Q/111Q}$ cells had a lower phospho-AKT/AKT ratio than wild-type cells (FIG. 7A). GM1 administration increased the phospho-AKT/AKT ratio, both in STHdh$^{7Q/7Q}$ and in STHdh$^{111Q/111Q}$ cells, an effect that was still measurable six hours after the application of apoptotic conditions. After GM1 administration, levels of active (phospho) AKT in STHdh$^{111Q/111Q}$ were restored to normal (FIG. 7A).

To further investigate the involvement of AKT in GM1-mediated neuroprotection, STHdh$^{111Q/111Q}$ cells were pre-incubated with triciribin (TCN), an inhibitor of AKT activation (Yang et al., 2004), before induction of apoptosis and treatment with GM1. TCN blocked the anti-apoptotic effect of GM1 only partly (FIG. 7B), suggesting that the neuroprotective action of GM1 is only partially dependent on AKT activation and that other pro-survival effects must be at play.

Figure 10:
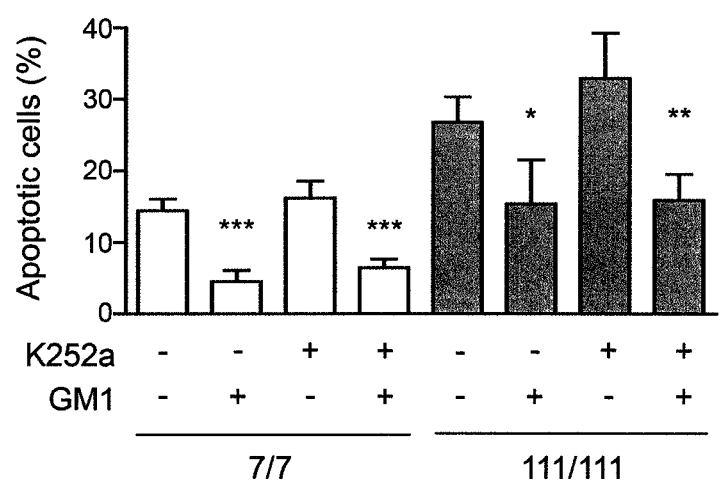
Figure 14:
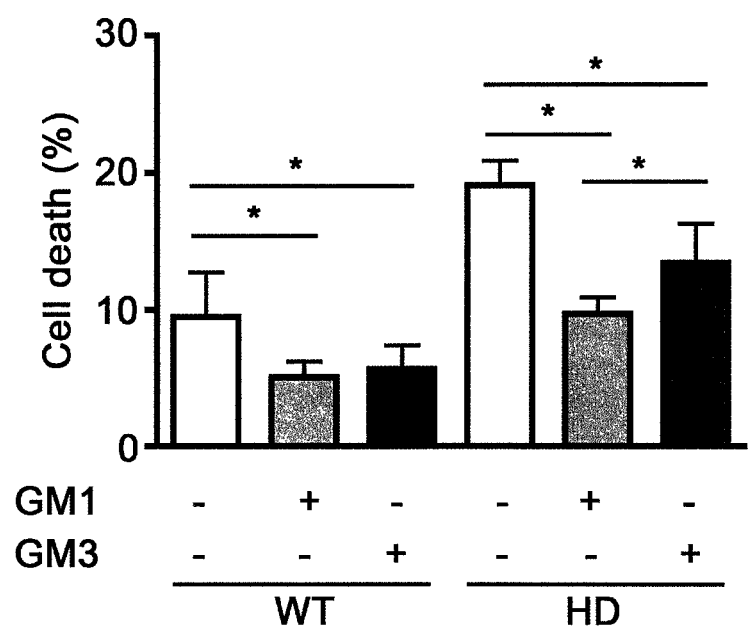
FIG. 14—GM3 protects HD cells from apoptosis. Immortalized knock-in striatal cells expressing wild-type (WT) or mutant (HD) huntingtin were exposed to apoptotic conditions (serum deprivation at 39° C.) in the absence or presence of 50 μM GM1 or 50 μM GM3. Quantitation of apoptotic cells was done by FACS analysis of Annexin V-binding. Data are the mean±SD of 2 experiments, each performed in triplicate.

It has been reported that GM1 administration increases activation of Trk receptors (Ferrari et al., 1995; Rabin et al., 2002). It was tested whether such a mechanism could account, at least in part, for the protection provided by GM1. In the presence of K252a, a pan-trk receptor inhibitor (Tapley et al., 1992), GM1 protective activity was still fully preserved indicating that the Trk receptor pathway is not involved in the anti-apoptotic effect of GM1 (FIG. 10).

GM1 Administration Promotes mHtt Phosphorylation.

Figure 8:
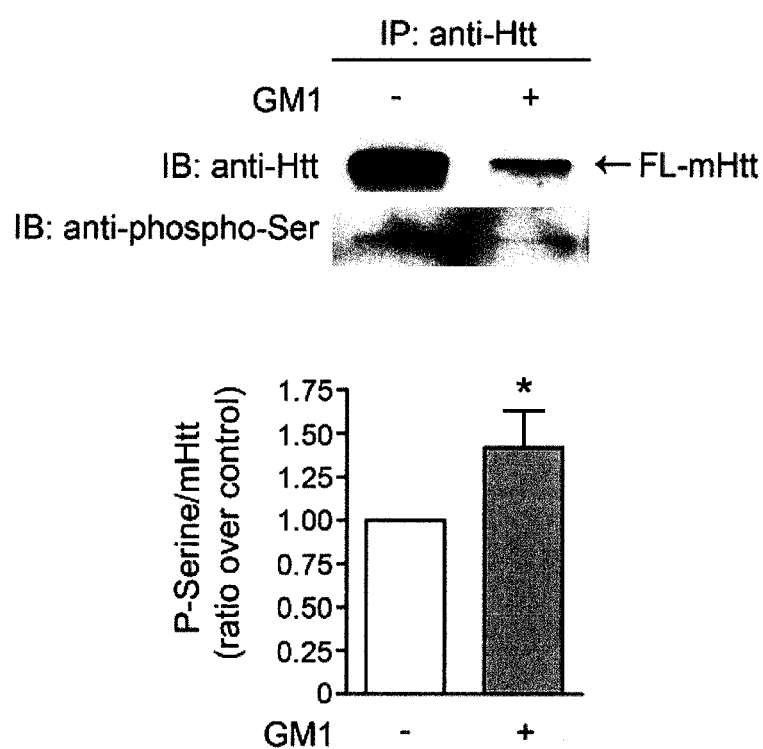

The phosphorylation state of mHtt upon cell treatment with GM1 was next examined. As shown in FIG. 8, administration of GM1 to STHdh$^{111Q/111Q}$ cells resulted in increased mHtt phosphorylation as assessed by mHtt immunoprecipitation and immunoblotting with an anti phospho-Ser antibody.

Discussion

In spite of being a monogenic disease, HD is a complex disorder resulting from a cascade of pathogenic events triggered by mHtt. Thus, one of the major challenges in the field is to discriminate between mere epiphenomena and dysfunctions that contribute to disease pathogenesis and progression.

It is shown herein that ganglioside GM1 levels are reduced in HD cells. Gangliosides have a plethora of functions in the brain (Ledeen and Wu, 2008; Mocchetti, 2005; Yu et al., 2009). GM1, in particular, is involved in signaling (Prinetti et al., 2009), neurite outgrowth (Abad-Rodriguez and Robotti, 2007; Ichikawa et al., 2009; Wu et al., 2007), and neurotransmission (Furuse et al., 1998; Wieraszko and Seifert, 1985). Therefore, as shown herein, while not wishing to be bound by theory, even a partial reduction of GM1 is likely to have a profound impact on the physiology of HD neurons. GM2/GD2 synthase null mice, which lack complex gangliosides (GM2, GM1, GD1a and GT1a), develop motor symptoms that are common to YAC128 HD mice, including hind limb clasping, impaired rotarod performance, reduced open field activity and catalepsy (Chiavegatto et al., 2000; Liu et al., 1999; Slow et al., 2003). In these mice, axonal degeneration and demyelination in the central nervous system and in the sciatic nerve precede motor problems by several months (Chiavegatto et al., 2000; Sheikh et al., 1999; Sun et al., 2004), a phenotype that is reminiscent of the early white matter dysfunction observed in pre-symptomatic HD patients (Ciarmiello et al., 2006) and R6/2 HD mice (Wade et al., 2008). Similarly to HD mouse models (Fan and Raymond, 2007), GM2/GD2 synthase null mice are also more susceptible to excitotoxic stimuli (Wu et al., 2005). Motor problems are already present in heterozygous GM2/GD2 synthase+/− mice (Chiavegatto et al., 2000), indicating that even a partial reduction of complex gangliosides is sufficient to induce neural dysfunction and neurodegeneration.

As described herein, plasma membrane and total levels of GM1 were significantly reduced in HD cells, in YAC128 striatum and cortex and in derived primary neurons. GM1 levels were lower in immortalized striatal cells expressing an N-terminal fragment of mHtt (N548-120Q) than in knock-in cells expressing endogenous levels of the full-length protein (STHdh$^{111Q/111Q}$).

In addition to GM1, GT1b and GD1a were also decreased in the striatum and cortex of YAC128 mice. GD1a serves as a reserve for the spatially-regulated generation of GM1 by the sialidase Neu3 (Miyagi et al., 2008) in various neural compartments (Da Silva et al., 2005; Tettamanti et al., 1972). In addition, and again not wishing to be bound by theory, since both GT1b and GD1a are ligands for the myelin associated glycoprotein (MAG) and play a role in myelin-axon adhesion and axon stability (Lopez and Schnaar, 2009), their deficit in HD is also likely to affect brain functions.

The present analyses were performed in 6 month-old mice, when animals were symptomatic but did not yet show signs of neurodegeneration (Slow et al., 2003). Therefore, the ganglioside profile herein described reflects the activity of metabolic pathways, rather than accumulation of reactive glia, loss of neurons or other factors that could potentially confound data interpretation (Seyfried and Yu, 1985). Reduced synthesis likely accounts for the reported decrease of specific gangliosides, as suggested by down-regulated B3galt4 (GM1/GD1b/GT1c synthase) expression in striatal cells and in human HD fibroblasts. The expression of other genes involved in the ganglioside biosynthetic pathway was also decreased in different areas of the brain in YAC128 mice. No differences in the expression of these genes between YAC128 and wild-type littermates were observed in the hippocampus, a brain region that is less affected in HD, suggesting that aberrant ganglioside metabolism may contribute to the region-specific neural dysfunction typical of the HD pathology.

Expression of the ganglioside biosynthetic enzymes is highly regulated in a cell and tissue-specific manner (Yu et al., 2004), however the underlying regulatory mechanisms are still unclear. Overall, the repressive effect exerted by mHtt might arise from its action on the transcription factor Sp1, which is involved in the transcription of most of the affected ganglioside biosynthetic genes (Yu et al., 2004), or on the cyclic-AMP-responsive element binding protein (CREB), which regulates transcription of the B3galt4 gene (Xia et al., 2003). In fact, the activity of both Sp1 and CREB has been shown to be impaired in several HD models (Dunah et al., 2002; Imarisio et al., 2008).

The present application demonstrates that GM1 is decreased in human skin fibroblasts derived from HD patients and thus, it represents a specific trait of the HD pathology. Since the dysfunction can be measured in peripheral cells, GM1 levels are a useful disease biomarker. In this regard, it is of note that one of the human fibroblast lines used in this study (HD50) was derived from an 11 year-old asymptomatic boy who developed the disease 15 years later (Coriell Repository data—cell line I.D. # GM04855). Hence, aberrant ganglioside metabolism was already manifested in peripheral tissues before clinical disease onset. HD fibroblasts expressing mHtt with the highest number of glutamines (HD86) had the lowest level of GM1/GD1b/GT1c synthase expression suggesting a potential correlation between the length of pathogenic polyQ stretches and extent of downregulation of the ganglioside biosynthetic pathway.

The instant application also demonstrates that even relatively small variations in the amount of plasma membrane GM1 may result in dramatic changes in HD cell susceptibility to apoptosis, and that administration of exogenous GM1 can restore ganglioside levels and cell survival. Importantly, the present experiment were able to reproduce the HD phenotype (in terms of susceptibility to apoptosis) in wild-type cells by pharmacologically reducing cellular GM1 content to the levels observed in HD cells. These data suggest that reduced amounts of GM1 in HD cells are causative of cell dysfunction, rather than an epiphenomenon.

Administration of GM1 to striatal cells resulted in the activation of the pro-survival kinase AKT. GM1 treatment abolished the difference in the phospho-AKT/AKT ratio between wild-type and HD cells. Also triggered by GM1 administration was the increase of mHtt phosphorylation. Because phospho-mHtt was detected with an anti-pSer antibody after Htt immunoprecipitation, it was not possible to establish which kinase/s was/were responsible for the phosphorylation of mHtt and at which site.

The instant application demonstrates that reduced synthesis of GM1 occurs in models of HD and in fibroblasts from HD patients, leading to increased susceptibility of HD cells to apoptosis. Administration of GM1 to HD cells restores normal cellular levels of the ganglioside and drastically increases survival, an effect that is at least in part mediated by restoration of AKT activation and leads to increased mHtt phosphorylation.

The neuroprotective effect of GM1 was partially dependent on AKT activation. An AKT inhibitor reduced GM1 protection, but did not abolish it. Therefore, while not wishing to be bound by theory, GM1 might have activated an additional pro-survival pathway or, alternatively, blocked a pro-apoptotic step. Increased mHtt phosphorylation by kinases other than AKT could also explain the AKT-independent additional protection. It has been proposed that in models of excitotoxicity and neurotoxicity, GM1 and its semi-synthetic analogue LIGA-20 exert neuroprotection by regulating (Prinetti et al., 2009) nuclear Ca++ homeostasis (Ledeen and Wu, 2008). However, LIGA-20, which had been shown to be at least an order of magnitude more potent than GM1 (Wu et al., 2004), was not effective in protecting striatal cells in the present study (FIG. 13). Interestingly, while one of the best-characterized effects of GM1 is its ability to modulate the activity of neurotrophin receptors, in our experimental conditions protection from apoptosis was achieved even in the presence of a pan-Trk receptor inhibitor.

In HD, where endogenous levels of the ganglioside are reduced, GM1 is likely to have multiple beneficial effects, by restoring normal ganglioside content and by targeting multiple aspects of the HD pathology: from cell signaling and AKT activation to mHtt phosphorylation, susceptibility to apoptosis, and potentially also axonal transport and neurotrophin release and excitotoxicity.

Previous clinical trials that have tested the effects of GM1 in patients with stroke (Alter, 1998), Parkinson's disease (Schneider, 1998) and spinal cord injury (Chinnock and Roberts, 2005) have shown that the compound is relatively safe to use. Possible potential adverse effects, such as the development of a peripheral neuropathy known as Guillain-Barre' syndrome (GBS) (Vucic et al., 2009) are rare (Alter, 1998) and the risk/benefit ratio might be acceptable in the case of HD.

Example II

Materials and Methods

Animal and Cell Models.

YAC128 mice were purchased from the Jackson Laboratories (Jackson Laboratories, Bar Harbor, Me., USA). YAC128 mice are one of the best characterized animal model of HD and express the entire human HD gene (promoter and entire coding sequence) with 128 CAG repeats, on FVB strain genetic background (Slow, E. J., et al. (2003)). These mice display an array of motor, behavioral and neuropathological deficits that recapitulate the human pathology (Slow, E. J., et al. (2003), Pouladi, M. A., et al. (2009), Van Raamsdonk, J. M., et al. (2007); Van Raamsdonk, J. M., (2006), Van Raamsdonk, J. M., (2005), Van Raamsdonk, J. M., et al. (2005)). Female YAC128 mice were crossed with male FVB/N wild-type mice for colony maintenance. All procedures on animals were approved by the University of Alberta's Animal Care and Use Committee and were in accordance with the guidelines of the Canadian Council on Animal Care.

Conditionally-immortalized mouse striatal knock-in cells expressing endogenous levels of mHtt (STHdh$^{111/111}$) were a gift from Dr. M. E. MacDonald (Massachusetts General Hospital, Boston, Mass., USA) and were maintained as previously described (Trettel, F., et al. (2000)). Human skin fibroblasts isolated from HD patients were purchased from the Coriell Cell Repositories (Coriell Institute for Medical Research, Camden, N.J., USA) and grown in modified Eagle's Medium (MEM, Invitrogen) supplemented with 15% fetal bovine serum (FBS), 2 mM L-glutamine, 100 U/mL penicillin, 100 µg/mL streptomicin and 0.11 g/L sodium pyruvate (all from Invitrogen).

Cultures of primary cortical neurons were prepared from newborn mice (P0). Briefly, the brain was dissected and selected regions were minced and digested with 1 mg/ml papain for 10 minutes at 37° C. DNAse was added to the digestion mix in the last 5 minutes of incubation. Cells were centrifuged at 200×g for 1 minute, resuspended in Neurobasal-A medium (Invitrogen) supplemented with 1% B27 (Invitrogen) and gently dissociated by pipetting up and down. Neurons were plated onto poly-D-lysine-coated wells at a density of $0.1 \times 10^6$ cells/cm$^2$ and used for experiments at 10-12 days in vitro.

Treatment with GM1 and Analysis of mHtt Phosphorylation by Microscopy.

Cells were seeded onto glass coverslips coated with 50 µg/ml poly-L-lysine. The day after, cells were treated with 50 µM GM1 for 5 hours, washed and fixed in 4% paraformaldehyde at room temperature (r.t.) for 10 minutes. After cell permeabilization with 0.1% Triton X-100 for 5 minutes, incubation with anti-phosphoSer13, phosphoser16 antibody (N17pS13pS16, kindly donated by Dr. Truant, McMaster University, Canada) was performed at 1:1000 dilution in PBS+4% donkey serum for 1 hour at r.t. Secondary antibody used were anti-rabbit Alexa-A488 (for knock-in cells and neurons) and anti-rabbit Alexa-A555 (for human fibroblasts), used at 1:500 dilution in PBS+4% donkey serum for 1 hour at r.t. After 3 washes, nuclei were counterstained with DAPI and the slides were mounted with ProLong Gold antifading reagent (Invitrogen). Analysis was performed with a Zeiss Axiovert 100 epifluorescent microscope or with a LSM510 laser scanning confocal microscope mounted on a Zeiss Axiovert 100M microscope (for fibroblasts). Images of wild-type and HD cells were acquired using the same confocal settings or same exposure time.

PPMP Treatment and Immunoblotting.

Knock-in striatal cells expressing wild-type Htt (7/7) or mHtt (111/111) (Trettel, F., et al. (2000)) were incubated for 3 days in medium containing 10 µM 1-phenyl-2-palmitoylamino-3-morpholino-1-propanol (PPMP, Matreya, Pleasant Gap, Pa., USA) to inhibit ganglioside synthesis. Cells were then washed two times with PBS and lysed in 50 mM Tris, 1% NP-40, 1 mM EDTA, 10 mM NaF, 1 mM $Na_2VO_4$ and 1:100 protease inhibitor cocktail (SIGMA-Aldrich). Proteins were resolved on 6% SDS-PAGE and immunoblotted with N17pS13pS16 antibody (1:1000) and anti-Htt (mAb2166, Millipore, 1:3000). HRP-conjugated secondary antibodies were used at 1:3,000 dilution (Bio-Rad Laboratories, Hercules, Calif., USA). Protein bands were detected by ECL Plus and quantitated with Quantity One® software (Bio-Rad Laboratories, Hercules, Calif., USA).

Chronic GM1 Infusion.

Five month-old mice were stereotaxically implanted with a cannula in the right brain lateral ventricle (Cho, S. R., et al. (2007)). The cannula was connected to a subcutaneous micro-osmotic pump (Alzet Model 2004) implanted on the back of the animal. The pump infused a solution of 5.6 mg GM1/ml in artificial cerebrospinal fluid (CSF) (or CSF only in control groups) into the brain ventricle at constant rate (0.25 µl/h, corresponding to 1.4 µg GM1/h or 33.6 µg GM1/day) for 28 days. Because the volume of mouse CSF is 35 µl and because the rate of synthesis/renewal of CSF in the mouse is 18 µl/h 15, the conditions listed above should result in a concentration of 50 µM GM1 in the mouse CSF (when equilibrium is reached a few hours later). Mice were let recovery for a week, after which motor behavior tests were performed on weekly bases.

Motor Behavior Analysis.

Motor behavior was evaluated with two sensitive tests that are considered the gold-standard for analysis of HD motor deficit: rotarod and horizontal ladder test (Ferrante, R. J. (2009)) To avoid that stress and anxiety would affect motor performance, mice were acclimatized for two days to training room, instruments and tasks to perform, before measuring the actual performance in each specific task. For the rotarod test, mice received 1-day training, followed by 3×60 sec-sessions/day, at a fixed rotarod speed (32 rpm), with 10 minute interval between sessions, over a period of three days. Latency to fall off the rotarod in each of these sessions was measured, averaged and compared across groups. For the horizontal ladder walking test, a task that assesses loss and recovery of sensorimotor functions 16, mice were recorded with a videocamera as they walked spontaneously across the ladder. The task difficulty level was adjusted by varying the position and the space between the metal rungs of the ladder (from 0.5 to 2.5 cm). An arbitrary score was assigned to the most type of errors (footfalls) committed by the mouse when performing this task. Each mouse underwent 1 session/day for 5 days and the scores accumulated in each session were averaged.

Analysis of Htt Phosphorylation in Tissue Isolated from GM1- and CSF-Infused Mice.

At the end of the GM1 infusion protocol (28 days after peristaltic pump implantation), mice were euthanized. Brain cortices were dissected and homogenized in 50 mM Tris, 1% NP40, 1 mM EDTA, 10 mM NaF, 1 mM $Na_2VO_4$ and 1:100 protease inhibitor cocktail (SIGMA-Aldrich). Proteins were resolved on 6% SDS-PAGE and immunoblotted with N17pS13pS16 antibody in Odyssey buffer (LiCor) (1:1000). Alexa680-conjugated secondary antibody were used at 1:1,000 dilution in Odyssey buffer. Imaging and analysis were performed using and Odyssey Infrared System (LiCor).

Results and Discussion

As shown above, levels of the ganglioside GM1 are decreased in cell and animal models of Huntington's disease (HD), as well as in fibroblasts from HD patients. Decreased GM1 levels contribute to heighten HD cell susceptibility to apoptosis. Administration of GM1 restores ganglioside levels in HD cells and promotes activation of AKT and phosphorylation of mutant huntingtin (Htt), leading to decreased mutant Htt toxicity and increased survival of HD cells.

GM1 Increases Phosphorylation of Htt at Amino Acid Residues that are Critical for Toxicity.

Figure 16:
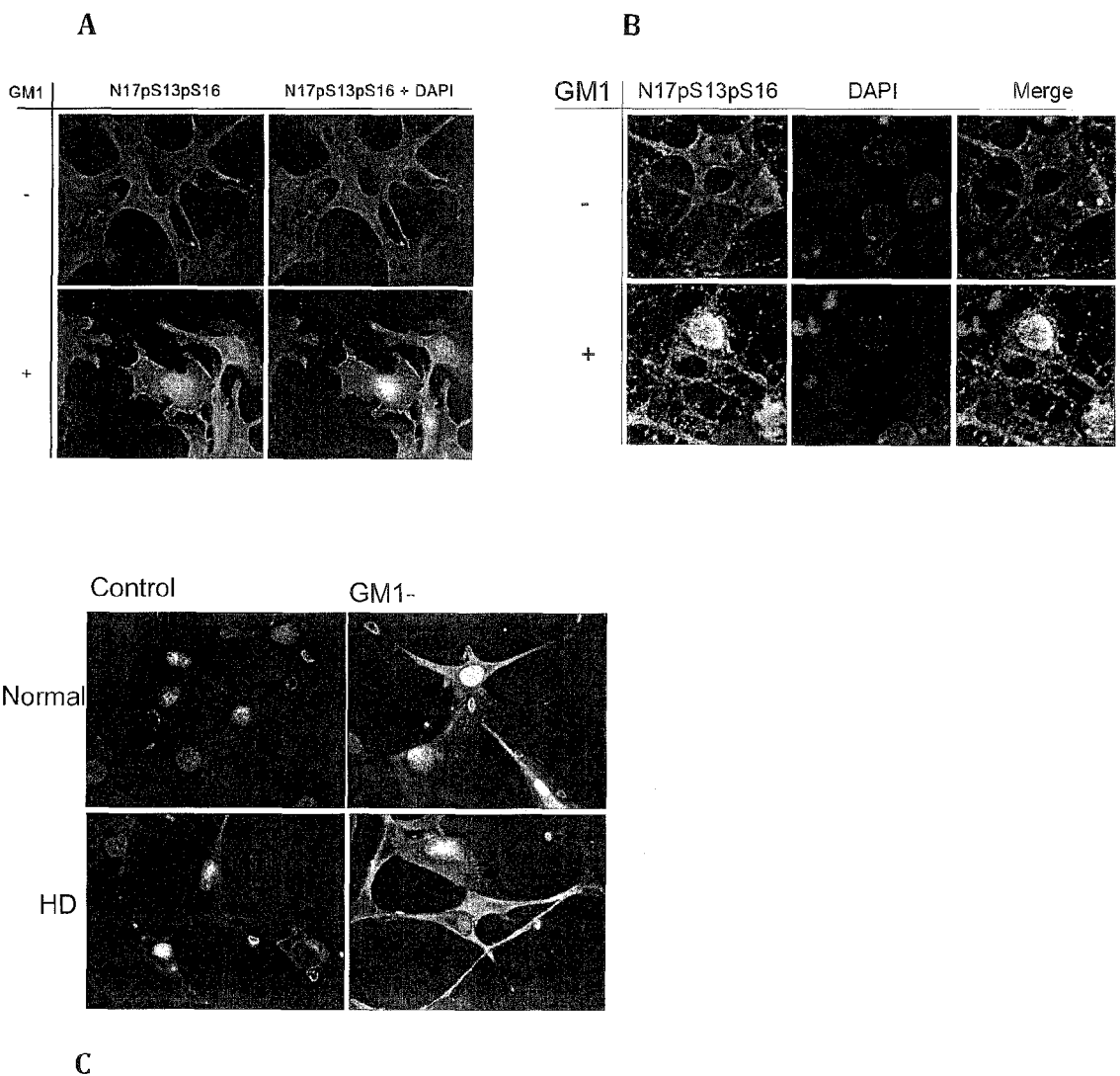
FIG. 16—GM1 increases phosphorylation of Htt at amino acid residues that are critical for toxicity. (Panel A) Immortalized striatal cells (111/1111) were incubated for 2 hours with or without GM1. Cells were fixed and immunostained with N17pS13pS16 antibody, which recognizes Htt phosphorylated at S13 and S16. Images were taken with an epifluorescence microscope using identical exposure time. (Panel B) Confocal microscopy images of YAC128 (HD) cortical neurons treated with or without GM1 for 2 hours. Cells were fixed and immunostained with N17pS13pS16 antibody (green), and counterstained with DAPI to identify nuclei. Images were acquired using the same confocal scanning parameters. (Panel C) Age-matched fibroblasts derived from normal subjects or HD patients were treated with or without GM1 for 2 hours. Cells were fixed and immunostained with N17pS13pS16 antibody (red), and counterstained with DAPI to identify nuclei. Images were taken with an epifluorescence microscope using identical exposure time.

In FIG. 16, Panel A, immortalized striatal cells (111/1111) were incubated for 2 hours with or without GM1. Cells were fixed and immunostained with N17pS13pS16 antibody, which recognizes Htt phosphorylated at S13 and S16. Images were taken with an epifluorescence microscope using identical exposure time. Increased cell immunoreactivity after GM1 treatment is shown. Panel B depicts confocal microscopy images of YAC128 (HD) cortical neurons treated with or without GM1 for 2 hours. Cells were fixed and immunostained with N17pS13pS16 antibody (green), and counterstained with DAPI to identify nuclei. Images were acquired using the same confocal scanning parameters. Panel C shows age-matched fibroblasts derived from normal subjects or HD patients treated with or without GM1 for 2 hours. Cells were fixed and immunostained with N17pS13pS16 antibody (red), and counterstained with DAPI to identify nuclei. Images were taken with an epifluorescence microscope using identical exposure time These data demonstrate that treatment with GM1 increases phosphorylation of Htt on Ser13 and Ser16 in cell lines, primary HD neurons and human fibroblasts derived from HD patients (FIGS. 16A, 16B and 16C), as determined by immunostaining with a phosphoSer13, phosphoS16-specific anti-Htt antibody.

Inhibition of Ganglioside Synthesis Causes a Decrease in Htt Phosphorylation at Ser13 and S16

Figure 17:
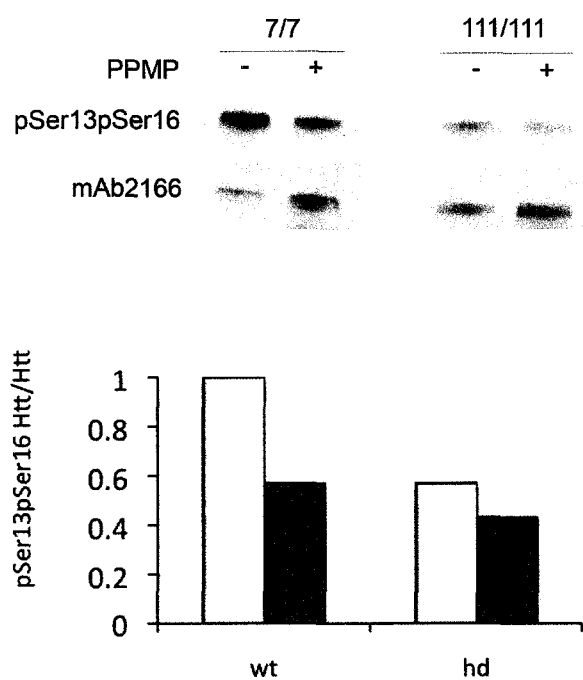
FIG. 17—Inhibition of ganglioside synthesis causes a decrease in Htt phosphorylation at Ser13 and S16. (Panel A) Synthesis of gangliosides was inhibited in striatal knock-in cells with PPMP. Levels of total and phospho-Htt were detected in total cell lysates with mAb2166 and N17pS13pS16 antibody, respectively. The graph is the densitometric analysis of the immunoblot showed.

FIG. 17 demonstrates inhibition of ganglioside cynthesis causes a decrease in Htt phosphorylation at Ser13 and S16. In these experiments, synthesis of gangliosides was inhibited in striatal knock-in cells with PPMP, as above. Levels of total and phospho-Htt were detected in total cell lysates using immunoblotting (Panel A) with mAb2166 and N17pS13pS16 antibody, respectively. Panel B is a graph is the densitometric analysis of the immunoblot show in Panel A.

Inhibition of ganglioside synthesis by PPMP decreases levels of phosphorylation at the same amino acid residues (FIG. 17). These data demonstrate a link between cellular GM1 levels and Htt phosphorylation. These data identify GM1 as a pharmacological treatment that has an effect on mHtt protein itself.

Analysis of Motor Behavior in YAC128 Mice Prior to GM1 Infusion.

To examine the neuroprotective role of GM1 in HD, a study in YAC128 mice, a well-characterized model of HD (Slow, E. J. et al, 2003), was undertaken, in which GM1 was administered by chronic intraventricular brain infusion for 28 days.

The motor behavior of five month-old YAC128 mice and wild-type littermates was analyzed using the rotarod and the horizontal ladder task (FIG. 18). Both tests are widely used to measure motor deficit in various models of neurodegeneration (Farr, T. D. et al. 2006), including HD (Fermate, R. J., 2009).

Rotarod performance in YAC128 and WT mice is depicted in FIG. 18, Panels A and B. In Panel A, five-month old YAC128 mice and WT littermates underwent 3 sessions/day (60 seconds each at 32 rpm) for 3 days. The graph in Panel A represents the average performance of 6 mice per genotype over 3 days of training. The photograph in Panel B depicts motor deficit in 6-month old YAC128 mouse, as compared to a WT mouse, is evident from their position on the rotarod.

The horizontal ladder task, a sensitive measure of motor deficits, is depicted in Panels C and D. Panel C shows the horizontal ladder, which was made of metal rungs, the pattern of which can be changed to increase task difficulty. Irregular patterns prevents the animal from learning the position of the rungs and highlights specific motor deficits. Panel D depicts the error scores of six month-old YAC128 mouse and WT mice. These data show YAC18 mice make more mistakes (deep and slight slips, total misses, etc.) than wild-type mice;

GM1 Infusion Restores Normal Motor Behavior in YAC128 Mice.

Before treatment with GM1, HD mice displayed significant motor deficits when tested on the rotarod and in the horizontal ladder task.

Seven days after the beginning of motor tests, the mice were stereotaxically implanted with a cannula in the right lateral ventricle, and connected to a subcutaneous microosmotic pump (Alzet Model 2004) implanted on the back of the animal. The pump infused a solution of 3.6 mg GM1/ml in artificial CSF (or CSF only in control groups) into the brain ventricle at constant rate (0.25 µl/h) for 4 weeks. The amount of GM1 infused was calculated in order to achieve 50 µM final concentration in the mouse CSF. This was the most effective (neuroprotective) GM1 concentration in the in cell studies supra. Three mice per genotype received GM1 and three received CSF only (control). All mice recovered well after surgery.

Motor behavior was tested again at various time-points after surgery, for a total of 4 weeks. To ensure unbiased analysis of the data experimenters were blind to the genotype of the animals for the entire length of the experimental protocol.

Behavioral tests showed that HD mice infused with GM1 performed significantly better than HD control mice infused with CSF. After 13 days of GM1 infusion HD mice became indistinguishable from wild-type mice (FIG. 19).

No behavioral differences were noted in wild-type mice, whether they were infused with CSF or GM1, suggesting that the ganglioside had HD-specific effects.

FIG. 19 depicts the results of (Panel A) the horizontal ladder task of YAC128 and WT littermates infused with CSF or GM1 which performed the horizontal ladder task for 3 days, starting at the indicated time after micropump implantation. The graph represents the average performance of 3 mice per group over 3 days of tests. *, p<0.05 (relative to YAC128 receiving CSF only). Panel B depicts Rotarod performance of YAC128 and WT littermates infused with CSF or GM1 which underwent 3 sessions/day (60 seconds each at 32 rpm) for 3 days, starting at the indicated time after micropump implantation. The graph represents the average performance of 3 mice per group over 3 days of training. *, p<0.05 (relative to YAC128 receiving CSF only).

Infusion Increases Huntingtin Phosphorylation in Vivo in YAC128 Mice.

Subsequent to the experimental protocol on animals described above, the mouse brains were dissected and homogenized to examine Htt phosphorylation at Ser13 and Ser16.

Figure 20:
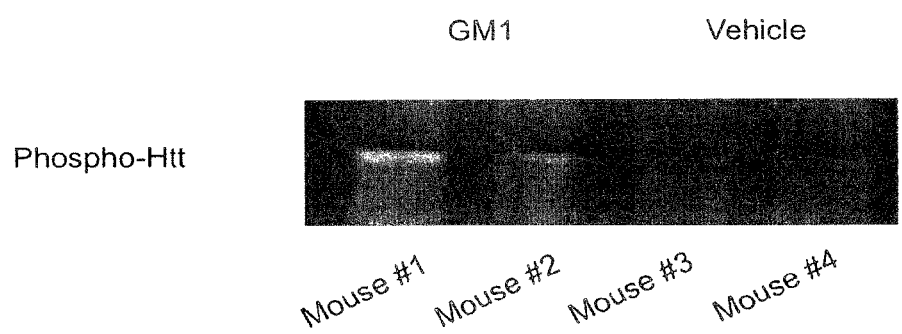
FIG. 20—GM1 infusion increases huntingtin phosphorylation in vivo in YAC128 mice (Panel A) YAC128 and WT littermates infused with CSF (vehicle) or GM1 for 28 days were sacrificed and the amount of phospho-Htt in the same amount of cerebral cortex homogenate was detected by immunoblotting with a pSer13Ser16 specific antibody.

In FIG. 20, YAC128 mice and WT littermates infused with CSF (vehicle) or GM1 for 28 days were sacrificed and the amount of phospho-Htt in the same amount of cerebral cortex homogenate was detected by immunoblotting with a pSer13Ser16 specific antibody. Mice treated with GM1 showed an increase in the phosphorylation of Htt at these residues, which makes mutant Htt less toxic.

REFERENCES (1993). A novel gene containing a trinucleotide repeat that is expanded and unstable on Huntington's disease chromosomes. The Huntington's Disease Collaborative Research Group. Cell 72, 971-983.

Abad-Rodriguez, J., and Robotti, A. (2007). Regulation of axonal development by plasma membrane gangliosides. J Neurochem 103 Suppl 1, 47-55.

Abe, A., Inokuchi, J., Jimbo, M., Shimeno, H., Nagamatsu, A., Shayman, J. A., Shukla, G. S., and Radin, N. S. (1992). Improved inhibitors of glucosylceramide synthase. J Biochem 111, 191-196.

Alter, M. (1998). GM1 ganglioside for acute ischemic stroke. Trial design issues. Ann N Y Acad Sci 845, 391-401.

Anne, S. L., Saudou, F., and Humbert, S. (2007). Phosphorylation of huntingtin by cyclin-dependent kinase 5 is induced by DNA damage and regulates wild-type and mutant huntingtin toxicity in neurons. J Neurosci 27, 7318-7328.

Bae, B. I., Xu, H., Igarashi, S., Fujimuro, M., Agrawal, N., Taya, Y., Hayward, S. D., Moran, T. H., Montell, C., Ross, C. A., et al. (2005). p53 Mediates Cellular Dysfunction and Behavioral Abnormalities in Huntington's Disease. Neuron 47, 29-41.

Cattaneo, E., and Conti, L. (1998). Generation and characterization of embryonic striatal conditionally immortalized ST14A cells. J Neurosci Res 53, 223-234.

Chiavegatto, S., Sun, J., Nelson, R. J., and Schnaar, R. L. (2000). A functional role for complex gangliosides: motor deficits in GM2/GD2 synthase knockout mice. Exp Neurol 166, 227-234.

Chinnock, P., and Roberts, I. (2005). Gangliosides for acute spinal cord injury. Cochrane Database Syst Rev, CD004444.

Cho, S. R., et al. Induction of neostriatal neurogenesis slows disease progression in a transgenic murine model of Huntington disease. J Clin Invest 117, 2889-2902 (2007).

Ciarmiello, A., Cannella, M., Lastoria, S., Simonelli, M., Frati, L., Rubinsztein, D. C., and Squitieri, F. (2006). Brain White-Matter Volume Loss and Glucose Hypometabolism Precede the Clinical Symptoms of Huntington's Disease. J Nucl Med 47, 215-222.

Clarke, G., Collins, R. A., Leavitt, B. R., Andrews, D. F., Hayden, M. R., Lumsden, C. J., and McInnes, R. R. (2000). A one-hit model of cell death in inherited neuronal degenerations. Nature 406, 195-199.

Colin, E., Regulier, E., Perrin, V., Durr, A., Brice, A., Aebischer, P., Deglon, N., Humbert, S., and Saudou, F. (2005). Akt is altered in an animal model of Huntington's disease and in patients. Eur J Neurosci 21, 1478-1488.

Da Silva, J. S., Hasegawa, T., Miyagi, T., Dotti, C. G., and Abad-Rodriguez, J. (2005). Asymmetric membrane ganglioside sialidase activity specifies axonal fate. Nat Neurosci 8, 606-615.

Desplats, P. A., Denny, C. A., Kass, K. E., Gilmartin, T., Head, S. R., Sutcliffe, J. G., Seyfried, T. N., and Thomas, E. A. (2007). Glycolipid and ganglioside metabolism imbalances in Huntington's disease. Neurobiol Dis 27, 265-277.

Duchemin, A. M., Ren, Q., Neff, N. H., and Hadjiconstantinou, M. (2008). GM1-induced activation of phosphatidylinositol 3-kinase: involvement of Trk receptors. J Neurochem 104, 1466-1477.

Dunah, A. W., Jeong, H., Griffin, A., Kim, Y. M., Standaert, D. G., Hersch, S. M., Mouradian, M. M., Young, A. B., Tanese, N., and Krainc, D. (2002). Sp1 and TAFII130 transcriptional activity disrupted in early Huntington's disease. Science 296, 2238-2243.

Fan, M. M., and Raymond, L. A. (2007). N-methyl-D-aspartate (NMDA) receptor function and excitotoxicity in Huntington's disease. Prog Neurobiol 81, 272-293.

Farr, T. D., Liu, L., Colwell, K. L., Whishaw, I. Q. & Metz, G. A. Bilateral alteration in stepping pattern after unilateral motor cortex injury: a new test strategy for analysis of skilled limb movements in neurological mouse models. J Neurosci Methods 153, 104-113 (2006)

Favaron, M., Manev, H., Alho, H., Bertolino, M., Ferret, B., Guidotti, A., and Costa, E. (1988). Gangliosides prevent glutamate and kainate neurotoxicity in primary neuronal cultures of neonatal rat cerebellum and cortex. Proc Natl Acad Sci USA 85, 7351-7355.

Ferrante, R. J. Mouse models of Huntington's disease and methodological considerations for therapeutic trials. Biochim Biophys Acta 1792, 506-520 (2009).

Ferrari, G., Anderson, B. L., Stephens, R. M., Kaplan, D. R., and Greene, L. A. (1995). Prevention of apoptotic neuronal death by GM1 ganglioside. Involvement of Trk neurotrophin receptors. J Biol Chem 270, 3074-3080.

Fishman, P. H., Max, S. R., Tallman, J. F., Brady, R. O., Maclaren, N. K., and Cornblath, M. (1975). Deficient Ganglioside Biosynthesis: a novel human sphingolipidosis. Science 187, 68-70.

Furuse, H., Waki, H., Kaneko, K., Fujii, S., Miura, M., Sasaki, H., Ito, K. I., Kato, H., and Ando, S. (1998). Effect of the mono- and tetra-sialogangliosides, GM1 and GQ1b, on long-term potentiation in the CA1 hippocampal neurons of the guinea pig. Exp Brain Res 123, 307-314.

Gauthier, L. R., Charrin, B. C., Borrell-Pages, M., Dompierre, J. P., Rangone, H., Cordelieres, F. P., De Mey, J., MacDonald, M. E., Lessmann, V., Humbert, S., and Saudou, F. (2004). Huntingtin controls neurotrophic support and survival of neurons by enhancing BDNF vesicular transport along microtubules. Cell 118, 127-138.

Graham, R. K., Deng, Y., Slow, E. J., Haigh, B., Bissada, N., Lu, G., Pearson, J., Shehadeh, J., Bertram, L., Murphy, Z., et al. (2006). Cleavage at the caspase-6 site is required for neuronal dysfunction and degeneration due to mutant huntingtin. Cell 125, 1179-1191.

Gu, X., et al. Serines 13 and 16 are critical determinants of full-length human mutant huntingtin induced disease pathogenesis in HD mice. Neuron 64, 828-840 (2009).

Hakomori Si, S. I. (2002). Inaugural Article: The glycosynapse. Proc Natl Acad Sci USA 99, 225-232.

Hickey, M. A., and Chesselet, M. F. (2003). Apoptosis in Huntington's disease. Prog Neuropsychopharmacol Biol Psychiatry 27, 255-265.

Holmgren, J., Lonnroth, I., Mansson, J., and Svennerholm, L. (1975). Interaction of cholera toxin and membrane GM1 ganglioside of small intestine. Proc Natl Acad Sci USA 72, 2520-2524.

Humbert, S., Bryson, E. A., Cordelieres, F. P., Connors, N. C., Datta, S. R., Finkbeiner, S., Greenberg, M. E., and Saudou, F. (2002). The IGF-1/Akt pathway is neuroprotective in Huntington's disease and involves Huntingtin phosphorylation by Akt. Dev Cell 2, 831-837.

Ichikawa, N., Iwabuchi, K., Kurihara, H., Ishii, K., Kobayashi, T., Sasaki, T., Hattori, N., Mizuno, Y., Hozumi, K., Yamada, Y., and Arikawa-Hirasawa, E. (2009). Binding of laminin-1 to monosialoganglioside GM1 in lipid rafts is crucial for neurite outgrowth. J Cell Sci 122, 289-299.

Imarisio, S., Carmichael, J., Korolchuk, V., Chen, C. W., Saiki, S., Rose, C., Krishna, G., Davies, J. E., Ttofi, E., Underwood, B. R., and Rubinsztein, D. C. (2008). Huntington's disease: from pathology and genetics to potential therapies. Biochem J 412, 191-209.

Kaplan, D. R., and Miller, F. D. (2000). Neurotrophin signal transduction in the nervous system. Curr Opin Neurobiol 10, 381-391.

Karten, B., Hayashi, H., Francis, G. A., Campenot, R. B., Vance, D. E., and Vance, J. E. (2005). Generation and function of astroglial lipoproteins from Niemann-Pick type C1-deficient mice. Biochem J 387, 779-788.

Ladisch, S., and Gillard, B. (1985). A solvent partition method for microscale ganglioside purification. Anal Biochem 146, 220-231.

Ledeen, R. W. (1978). Ganglioside structures and distribution: are they localized at the nerve ending? J Supramol Struct 8, 1-17.

Ledeen, R. W., and Wu, G. (2008). Nuclear sphingolipids: metabolism and signaling. J Lipid Res 49, 1176-1186.

Ledeen, R. W., and Yu, R. K. (1982). Gangliosides: structure, isolation, and analysis. Methods Enzymol 83, 139-191.

Lievens, J. C., Rival, T., Iche, M., Chneiweiss, H., and Birman, S. (2005). Expanded polyglutamine peptides disrupt EGF receptor signaling and glutamate transporter expression in Drosophila. Hum Mol Genet 14, 713-724.

Liu, Y., Wada, R., Kawai, H., Sango, K., Deng, C., Tai, T., McDonald, M. P., Araujo, K., Crawley, J. N., Bierfreund, U., et al. (1999). A genetic model of substrate deprivation therapy for a glycosphingolipid storage disorder. J Clin Invest 103, 497-505.

Lopez, P. H., and Schnaar, R. L. (2009). Gangliosides in cell recognition and membrane protein regulation. Curr Opin Struct Biol.

Luo, S., Vacher, C., Davies, J. E., and Rubinsztein, D. C. (2005). Cdk5 phosphorylation of huntingtin reduces its cleavage by caspases: implications for mutant huntingtin toxicity. J Cell Biol 169, 647-656.

Mangiarini, L., Sathasivam, K., Seller, M., Cozens, B., Harper, A., Hetherington, C., Lawton, M., Trottier, Y., Lehrach, H., Davies, S. W., and Bates, G. P. (1996). Exon 1 of the HD gene with an expanded CAG repeat is sufficient to cause a progressive neurological phenotype in transgenic mice. Cell 87, 493-506.

Max, S. R., Maclaren, N. K., Brady, R. O., Bradley, R. M., Rennels, M. B., Tanaka, J., Garcia, J. H., and Cornblath, M. (1974). GM3 (hematoside) sphingolipodystrophy. N Engl J Med 291, 929-931.

Miyagi, T., Wada, T., Yamaguchi, K., Hata, K., and Shiozaki, K. (2008). Plasma membrane-associated sialidase as a crucial regulator of transmembrane signalling. J Biochem 144, 279-285.

Mocchetti, I. (2005). Exogenous gangliosides, neuronal plasticity and repair, and the neurotrophins. Cell Mol Life Sci 62, 2283-2294.

Oblinger, J. L., Boardman, C. L., Yates, A. J., and Burry, R. W. (2003). Domain-dependent modulation of PDGFRbeta by ganglioside GM1. J Mol Neurosci 20, 103-114.

Oppenheimer, S. (1990). GM1 ganglioside therapy in acute ischemic stroke. Stroke 21, 825.

Pardridge, W. Transnasal and intraventricular delivery. in Peptide drug delivery to the brain 112 (Raven Press, 1991).

Pope-Coleman, A., Tinker, J. P., and Schneider, J. S. (2000). Effects of GM1 ganglioside treatment on pre- and postsynaptic dopaminergic markers in the striatum of parkinsonian monkeys. Synapse 36, 120-128.

Pouladi, M. A., et al. Prevention of depressive behaviour in the YAC128 mouse model of Huntington disease by mutation at residue 586 of huntingtin. Brain 132, 919-932 (2009).

Prinetti, A., Loberto, N., Chigorno, V., and Sonnino, S. (2009). Glycosphingolipid behaviour in complex membranes. Biochim Biophys Acta 1788, 184-193.

Van Raamsdonk, J. M., et al. Phenotypic abnormalities in the YAC128 mouse model of Huntington disease are penetrant on multiple genetic backgrounds and modulated by strain. Neurobiol Dis 26, 189-200 (2007).

Van Raamsdonk, J. M., Pearson, J., Murphy, Z., Hayden, M. R. & Leavitt, B. R. Wild-type huntingtin ameliorates striatal neuronal atrophy but does not prevent other abnormalities in the YAC128 mouse model of Huntington disease. BMC Neurosci 7, 80 (2006).

Van Raamsdonk, J. M., Murphy, Z., Slow, E. J., Leavitt, B. R. & Hayden, M. R. Selective degeneration and nuclear localization of mutant huntingtin in the YAC128 mouse model of Huntington disease. Hum Mol Genet 14, 3823-3835 (2005).

Van Raamsdonk, J. M., et al. Cognitive dysfunction precedes neuropathology and motor abnormalities in the YAC128 mouse model of Huntington's disease. J Neurosci 25, 4169-4180 (2005).

Rabin, S. J., Bachis, A., and Mocchetti, I. (2002). Gangliosides activate Trk receptors by inducing the release of neurotrophins. J Biol Chem 277, 49466-49472.

Rangone, H., Poizat, G., Troncoso, J., Ross, C. A., MacDonald, M. E., Saudou, F., and Humbert, S. (2004). The serum- and glucocorticoid-induced kinase SGK inhibits mutant huntingtin-induced toxicity by phosphorylating serine 421 of huntingtin. Eur J Neurosci 19, 273-279.

Rigamonti, D., Sipione, S., Goffredo, D., Zuccato, C., Fossale, E., and Cattaneo, E. (2001). Huntingtin's neuroprotective activity occurs via inhibition of procaspase-9 processing. J Biol Chem 276, 14545-14548.

Saito, M., Berg, M. J., Guidotti, A., and Marks, N. (1999). Gangliosides attenuate ethanol-induced apoptosis in rat cerebellar granule neurons. Neurochem Res 24, 1107-1115.

Schilling, B., Gafni, J., Torcassi, C., Cong, X., Row, R. H., LaFevre-Bernt, M. A., Cusack, M. P., Ratovitski, T., Hirschhorn, R., Ross, C. A., et al. (2006). Huntingtin phosphorylation sites mapped by mass spectrometry. Modulation of cleavage and toxicity. J Biol Chem 281, 23686-23697.

Schneider, J. S. (1998). GM1 ganglioside in the treatment of Parkinson's disease. Ann N Y Acad Sci 845, 363-373.

Sciannamblo, M., Chigorno, V., Passi, A., Valaperta, R., Zucchi, I., and Sonnino, S. (2002). Changes of the ganglioside pattern and content in human fibroblasts by high density cell population subculture progression. Glycoconj J 19, 181-186.

Seyfried, T. N., and Yu, R. K. (1985). Ganglioside GD3: structure, cellular distribution, and possible function. Mol Cell Biochem 68, 3-10.

Sheikh, K. A., Sun, J., Liu, Y., Kawai, H., Crawford, T. O., Proia, R. L., Griffin, J. W., and Schnaar, R. L. (1999). Mice lacking complex gangliosides develop Wallerian degeneration and myelination defects. Proc Natl Acad Sci USA 96, 7532-7537.

Simpson, M. A., Cross, H., Proukakis, C., Priestman, D. A., Neville, D. C., Reinkensmeier, G., Wang, H., Wiznitzer, M., Gurtz, K., Verganelaki, A., et al. (2004). Infantile-onset symptomatic epilepsy syndrome caused by a homozygous loss-of-function mutation of GM3 synthase. Nat Genet 36, 1225-1229.

Singhrao, S. K., Thomas, P., Wood, J. D., MacMillan, J. C., Neal, J. W., Harper, P. S., and Jones, A. L. (1998). Huntingtin protein colocalizes with lesions of neurodegenerative diseases: An investigation in Huntington's, Alzheimer's, and Pick's diseases. Exp Neurol 150, 213-222.

Sipione, S., Rigamonti, D., Valenza, M., Zuccato, C., Conti, L., Pritchard, J., Kooperberg, C., Olson, J. M., and Cattaneo, E. (2002). Early transcriptional profiles in huntingtin-inducible striatal cells by microarray analyses. Hum Mol Genet 11, 1953-1965.

Slow, E. J., van Raamsdonk, J., Rogers, D., Coleman, S. H., Graham, R. K., Deng, Y., Oh, R., Bissada, N., Hossain, S. M., Yang, Y. Z., et al. (2003). Selective striatal neuronal loss in a YAC128 mouse model of Huntington disease. Hum Mol Genet 12, 1555-1567.

Song, C., Perides, G., and Liu, Y. F. (2002). Expression of full-length polyglutamine-expanded Huntingtin disrupts growth factor receptor signaling in rat pheochromocytoma (PC12) cells. J Biol Chem 277, 6703-6707.

Sonnino, S., Mauri, L., Chigorno, V., and Prinetti, A. (2007). Gangliosides as components of lipid membrane domains. Glycobiology 17, 1R-13R.

Squitieri, F., Frati, L., Ciarmiello, A., Lastoria, S., and Quarrell, O. (2006). Juvenile Huntington's disease: does a dosage-effect pathogenic mechanism differ from the classical adult disease? Mech Ageing Dev 127, 208-212.

Stine, O. C., Pleasant, N., Franz, M. L., Abbott, M. H., Folstein, S. E., and Ross, C. A. (1993). Correlation between the onset age of Huntington's disease and length of the trinucleotide repeat in IT-15. Hum Mol Genet 2, 1547-1549.

Sun, J., Shaper, N. L., Itonori, S., Heffer-Lauc, M., Sheikh, K. A., and Schnaar, R. L. (2004). Myelin-associated glycoprotein (Siglec-4) expression is progressively and selectively decreased in the brains of mice lacking complex gangliosides. Glycobiology 14, 851-857.

Svennerholm, L. (1957). Quantitative estimation of sialic acids. II. A colorimetric resorcinol-hydrochloric acid method. Biochim Biophys Acta 24, 604-611.

Tapley, P., Lamballe, F., and Barbacid, M. (1992). K252a is a selective inhibitor of the tyrosine protein kinase activity of the trk family of oncogenes and neurotrophin receptors. Oncogene 7, 371-381.

Tettamanti, G. (2004). Ganglioside/glycosphingolipid turnover: new concepts. Glycoconj J 20, 301-317.

Tettamanti, G., Morgan, I. G., Gombos, G., Vincendon, G., and Mandel, P. (1972). Sub-synaptosomal localization of brain particulate neuraminidose. Brain Res 47, 515-518.

Toledo, M. S., Suzuki, E., Handa, K., and Hakomori, S. (2005). Effect of ganglioside and tetraspanins in microdomains on interaction of integrins with fibroblast growth factor receptor. J Biol Chem 280, 16227-16234.

Trettel, F., Rigamonti, D., Hilditch-Maguire, P., Wheeler, V. C., Sharp, A. H., Persichetti, F., Cattaneo, E., and MacDonald, M. E. (2000). Dominant phenotypes produced by the HD mutation in STHdh(Q111) striatal cells. Hum Mol Genet 9, 2799-2809.

Vucic, S., Kiernan, M. C., and Cornblath, D. R. (2009). Guillain-Barre syndrome: an update. J Clin Neurosci 16, 733-741.

Vyas, A. A., Patel, H. V., Fromholt, S. E., Heffer-Lauc, M., Vyas, K. A., Dang, J., Schachner, M., and Schnaar, R. L. (2002). Gangliosides are functional nerve cell ligands for myelin-associated glycoprotein (MAG), an inhibitor of nerve regeneration. Proc Natl Acad Sci USA 99, 8412-8417.

Wade, A., Jacobs, P., and Morton, A. J. (2008). Atrophy and degeneration in sciatic nerve of presymptomatic mice carrying the Huntington's disease mutation. Brain Res 1188, 61-68.

Walker, F. O. (2007). Huntington's disease. Lancet 369, 218-228.

Warby, S. C., Chan, E. Y., Metzler, M., Gan, L., Singaraja, R. R., Crocker, S. F., Robertson, H. A., and Hayden, M. R. (2005). Huntingtin phosphorylation on serine 421 is significantly reduced in the striatum and by polyglutamine expansion in vivo. Hum Mol Genet 14, 1569-1577.

Warby, S. C., Doty, C. N., Graham, R. K., Shively, J., Singaraja, R. R., and Hayden, M. R. (2009). Phosphorylation of huntingtin reduces the accumulation of its nuclear fragments. Mol Cell Neurosci 40, 121-127.

Wieraszko, A., and Seifert, W. (1985). The role of monosialoganglioside GM1 in the synaptic plasticity: in vitro study on rat hippocampal slices. Brain Res 345, 159-164.

Wu, G., Lu, Z. H., Obukhov, A. G., Nowycky, M. C., and Ledeen, R. W. (2007). Induction of calcium influx through TRPC5 channels by cross-linking of GM1 ganglioside associated with alpha5beta1 integrin initiates neurite outgrowth. J Neurosci 27, 7447-7458.

Wu, G., Lu, Z. H., Wang, J., Wang, Y., Xie, X., Meyenhofer, M. F., and Ledeen, R. W. (2005). Enhanced susceptibility to kainate-induced seizures, neuronal apoptosis, and death in mice lacking gangliotetraose gangliosides: protection with LIGA 20, a membrane-permeant analog of GM1. J Neurosci 25, 11014-11022.

Wu, G., Lu, Z. H., Xie, X., and Ledeen, R. W. (2004). Susceptibility of cerebellar granule neurons from GM2/GD2 synthase-null mice to apoptosis induced by glutamate excitotoxicity and elevated KCl: rescue by GM1 and LIGA20. Glycoconj J 21, 305-313.

Wu, G., Xie, X., Lu, Z. H., and Ledeen, R. W. (2001). Cerebellar neurons lacking complex gangliosides degenerate in the presence of depolarizing levels of potassium. Proc Natl Acad Sci USA 98, 307-312.

Xia, T., Gao, L., Yu, R. K., and Zeng, G. (2003). Characterization of the promoter and the transcription factors for the mouse UDP-Gal:betaGlcNAc beta1,3-galactosyltransferase gene. Gene 309, 117-123.

Yang, L., Dan, H. C., Sun, M., Liu, Q., Sun, X. M., Feldman, R. I., Hamilton, A. D., Polokoff, M., Nicosia, S. V., Herlyn, M., et al. (2004). Akt/protein kinase B signaling inhibitor-2, a selective small molecule inhibitor of Akt signaling with antitumor activity in cancer cells overexpressing Akt. Cancer Res 64, 4394-4399.

Yoon, S. J., Nakayama, K., Hikita, T., Handa, K., and Hakomori, S. I. (2006). Epidermal growth factor receptor tyrosine kinase is modulated by GM3 interaction with N-linked GlcNAc termini of the receptor. Proc Natl Acad Sci USA 103, 18987-18991.

Yu, R. K., Bieberich, E., Xia, T., and Zeng, G. (2004). Regulation of ganglioside biosynthesis in the nervous system. J Lipid Res 45, 783-793.

Yu, R. K., Nakatani, Y., and Yanagisawa, M. (2009). The role of glycosphingolipid metabolism in the developing brain. J Lipid Res 50 Suppl, S440-445.

Zala, D., Colin, E., Rangone, H., Liot, G., Humbert, S., and Saudou, F. (2008). Phosphorylation of mutant huntingtin at S421 restores anterograde and retrograde transport in neurons. Hum Mol Genet 17, 3837-3846.

Zuccato, C., Ciammola, A., Rigamonti, D., Leavitt, B. R., Goffredo, D., Conti, L., MacDonald, M. E., Friedlander, R. M., Silani, V., Hayden, M. R., et al. (2001). Loss of huntingtin-mediated BDNF gene transcription in Huntington's disease. Science 293, 493-498.

All publications, patents and patent applications mentioned in this Specification are indicative of the level of skill those skilled in the art to which this invention pertains and are herein incorporated by reference to the same extent as if each individual publication patent, or patent application was specifically and individually indicated to be incorporated by reference.

The invention being thus described, it will be obvious that the same may be varied in many ways. Such variations are not to be regarded as a departure from the spirit and scope of the invention, and all such modification as would be obvious to one skilled in the art are intended to be included within the scope of the following claims.

The embodiments of the invention in which an exclusive property or privilege is claimed are defined as follows:

1. A method of treating a motor symptom of Huntington's disease (HD) in a human subject suffering from HD, wherein said subject has a mutation in the HD gene and has exhibited at least one symptom of HD, said method comprising administering to said subject a therapeutically effective amount of ganglioside GM1.

2. The method of claim 1, wherein said administering comprises administration of GM1 into the cerebrospinal fluid of said subject.

3. The method of claim 2, wherein said administering comprises intrathecal delivery, intracerebroventricular delivery, or intraparenchymal delivery.

4. The method of claim 2, wherein said administering comprises intracerebroventricular delivery.

5. The method of claim 1, wherein said administration comprises intraperitoneal delivery, intramuscular delivery or subcutaneous delivery.

6. The method of claim 1, wherein said motor symptom is at least one of: chorea, hypokinesia, motor manifestations, motor impersistence, facial grimacing, ataxia, and dystonia.

7. The method of claim 1 wherein said treatment comprises increasing the survival time of the subject.

8. The method of claim 1, wherein a GM1 concentration of about 50 μM in the CSF of said subject is reached following said administration.

9. The method of claim 1, wherein said GM1 is naturally derived or synthetic.

10. The method of claim 1, wherein administration of said therapeutically effective amount of GM1 causes an increase in mHtt phosphorylation in said subject.

* * * * *